(12) United States Patent
Lazarovitz et al.

(10) Patent No.: US 6,716,252 B2
(45) Date of Patent: Apr. 6, 2004

(54) PROSTATIC STENT WITH LOCALIZED TISSUE ENGAGING ANCHORING MEANS AND METHODS FOR INHIBITING OBSTRUCTION OF THE PROSTATIC URETHRA

(75) Inventors: Jacob Lazarovitz, Hod Hasharon (IL); Iulian Cioanta, Cary, NC (US); Richard Barry Klein, Cary, NC (US)

(73) Assignee: WIT IP Corporation, Southborough, MA (US)

( * ) Notice: Subject to any disclaimer, the term of this patent is extended or adjusted under 35 U.S.C. 154(b) by 0 days.

(21) Appl. No.: 09/837,486

(22) Filed: Apr. 18, 2001

(65) Prior Publication Data

US 2002/0032486 A1 Mar. 14, 2002

Related U.S. Application Data

(60) Provisional application No. 60/215,156, filed on Jun. 30, 2000.

(51) Int. Cl.$^7$ .............................. A61F 2/04; A61M 5/00; A61M 29/00
(52) U.S. Cl. ....................... 623/23.66; 604/8; 604/96.01
(58) Field of Search .............................. 623/1.11, 23.66; 604/101.01–101.05, 102.01–102.03, 103, 103.01–103.08, 96.01, 104, 8, 9, 164.02, 247, 264, 27, 30; 606/108

(56) References Cited

U.S. PATENT DOCUMENTS

| | | |
|---|---|---|
| 1,652,954 A | 12/1927 | Pierce |
| 2,693,191 A | 11/1954 | Raiche |
| 3,625,793 A | 12/1971 | Sheridan et al. ............. 156/229 |
| 3,811,450 A | 5/1974 | Lord ........................ 128/349 R |
| 3,825,013 A | 7/1974 | Craven ..................... 128/349 B |
| 3,938,529 A | 2/1976 | Gibbons ..................... 128/349 |
| 4,137,922 A | 2/1979 | Leininger et al. ........... 128/344 |
| 4,183,102 A | 1/1980 | Guiset ............................. 3/1.4 |
| 4,407,271 A | 10/1983 | Schiff ........................ 128/1 D |
| 4,498,473 A | 2/1985 | Gereg .................. 128/207.15 |
| 4,610,660 A | 9/1986 | Rosenberg ................... 604/49 |
| 4,627,837 A | 12/1986 | Gonzalo ..................... 604/101 |
| 4,655,746 A | 4/1987 | Daniels et al. ................ 604/53 |
| 4,671,795 A | 6/1987 | Mulchin ..................... 604/281 |
| 4,686,985 A | 8/1987 | Lottick ........................ 128/344 |
| 4,693,704 A | 9/1987 | Ogita .......................... 604/55 |
| 4,710,169 A | 12/1987 | Christopher |
| 4,762,130 A | 8/1988 | Fogarty et al. ........... 128/348.1 |
| 4,776,337 A | 10/1988 | Palmaz ....................... 128/343 |
| 4,793,351 A | 12/1988 | Landman et al. ........... 128/344 |
| 4,819,751 A | 4/1989 | Shimada et al. ............ 128/344 |

(List continued on next page.)

FOREIGN PATENT DOCUMENTS

| | | | |
|---|---|---|---|
| EP | 0341988 B1 | 11/1989 | |
| EP | 058155 A1 | 9/1994 | |
| EP | 0582155 | 9/1994 | ......... A61M/25/00 |

(List continued on next page.)

OTHER PUBLICATIONS

PCT International Search Report, International Application No. PCT/US01/15585 dated Jun. 3, 2002.
International Search Report, International Application No. PCT/US01/15585, mailed May 2, 2002.

(List continued on next page.)

Primary Examiner—Corrine McDermott
Assistant Examiner—Alvin Stewart
(74) Attorney, Agent, or Firm—Ganz Law, P.C.; Bradley M. Ganz; James L. Wolfe

(57) ABSTRACT

A prostatic stent is configured as a unitary body, which is adapted to reside above the sphincter when in position in a subject and allow normal functioning of the sphincter. The stent includes and elongated and substantially narrow conduit, which extends through the sphincter and outside the body of the subject. The conduit is sized and constructed to allow normal operation of the sphincter. The stent also includes and upper and/or an intermediate inflatable portions and may include a second conduit for the introduction of medication to the stent.

22 Claims, 19 Drawing Sheets

U.S. PATENT DOCUMENTS

| | | | |
|---|---|---|---|
| 4,823,812 A | 4/1989 | Eshel et al. | 128/804 |
| 4,878,901 A | 11/1989 | Sachse | 604/174 |
| 4,893,623 A | 1/1990 | Rosenbluth | 604/282 |
| 4,900,314 A | 2/1990 | Quackenbush | 604/282 |
| 4,932,938 A | 6/1990 | Goldberg et al. | 604/96 |
| 4,932,956 A | 6/1990 | Reddy et al. | 606/192 |
| 4,946,449 A | 8/1990 | Davis, Jr. | 604/256 |
| 4,950,227 A | 8/1990 | Savin et al. | 604/8 |
| 4,955,859 A | 9/1990 | Zilber | 604/8 |
| 4,973,301 A | 11/1990 | Nissenkorn | 604/8 |
| 4,979,948 A | 12/1990 | Geddes et al. | 606/33 |
| 4,983,167 A | 1/1991 | Sahota | 606/194 |
| 4,994,066 A | 2/1991 | Voss | 606/108 |
| 4,995,872 A | 2/1991 | Ferrara | 604/280 |
| 5,007,437 A | 4/1991 | Sterzer | 428/786 |
| 5,007,898 A | 4/1991 | Rosenbluth et al. | 604/54 |
| 5,019,075 A | 5/1991 | Spears et al. | 606/7 |
| 5,041,092 A | 8/1991 | Barwick | 604/104 |
| 5,059,169 A | 10/1991 | Zilber | 604/8 |
| 5,087,244 A | 2/1992 | Wolinsky et al. | 604/53 |
| 5,098,374 A | 3/1992 | Othel-Jacobsen et al. | 604/8 |
| 5,098,379 A | 3/1992 | Conway et al. | 604/51 |
| 5,102,402 A | 4/1992 | Dror et al. | 604/265 |
| 5,112,306 A | 5/1992 | Burton et al. | 604/101 |
| 5,151,100 A | 9/1992 | Abele et al. | 606/28 |
| 5,163,906 A | 11/1992 | Ahmadi | 604/101 |
| 5,176,626 A | 1/1993 | Soehendra | 604/8 |
| 5,181,911 A | 1/1993 | Shturman | 604/96 |
| 5,188,596 A | 2/1993 | Condon et al. | 604/101 |
| 5,192,289 A | 3/1993 | Jessen | 606/155 |
| 5,220,927 A | 6/1993 | Astrahan et al. | 128/785 |
| 5,257,977 A | 11/1993 | Eshel | 604/113 |
| 5,269,802 A | 12/1993 | Garber | 606/191 |
| 5,286,259 A | 2/1994 | Ganguly et al. | 604/96 |
| 5,295,959 A | 3/1994 | Gurbel et al. | 604/96 |
| 5,306,241 A | 4/1994 | Samples | 604/54 |
| 5,308,356 A | 5/1994 | Blackshear, Jr. et al. | 606/194 |
| 5,312,430 A | 5/1994 | Rosenbluth et al. | 606/192 |
| 5,314,443 A | 5/1994 | Rudnick | 606/192 |
| 5,322,501 A * | 6/1994 | Mahmud-Durrani | 604/8 |
| 5,338,302 A | 8/1994 | Hasson | 604/105 |
| 5,372,600 A | 12/1994 | Beyar et al. | 606/108 |
| 5,383,856 A | 1/1995 | Bersin | 604/101 |
| 5,391,196 A | 2/1995 | Devonec | 607/96 |
| 5,419,763 A | 5/1995 | Hildebrand | 604/54 |
| 5,439,446 A | 8/1995 | Barry | 604/96 |
| 5,451,218 A | 9/1995 | Moore | 604/317 |
| 5,453,090 A | 9/1995 | Martinez et al. | 604/53 |
| 5,478,349 A | 12/1995 | Nicholas | 606/198 |
| 5,484,411 A | 1/1996 | Inderbitzen et al. | 604/96 |
| 5,499,994 A * | 3/1996 | Tihon et al. | 606/192 |
| 5,514,178 A | 5/1996 | Torchio | 623/12 |
| 5,518,498 A | 5/1996 | Lindenberg et al. | 600/30 |
| 5,521,392 A | 5/1996 | Kennedy et al. | 250/492.1 |
| 5,527,336 A | 6/1996 | Rosenbluth et al. | 606/192 |
| 5,545,132 A | 8/1996 | Fagan et al. | 604/96 |
| 5,549,559 A | 8/1996 | Eshel | 604/113 |
| 5,554,119 A | 9/1996 | Harrison et al. | 604/96 |
| 5,588,965 A | 12/1996 | Burton et al. | 604/101 |
| 5,593,412 A | 1/1997 | Martinez et al. | 606/108 |
| 5,609,583 A | 3/1997 | Hakki et al. | 604/282 |
| 5,669,930 A | 9/1997 | Igarashi | 606/191 |
| 5,685,847 A | 11/1997 | Barry | 604/96 |
| 5,718,680 A | 2/1998 | Kraus et al. | 604/53 |
| 5,718,686 A | 2/1998 | Davis | 604/101 |
| 5,725,547 A | 3/1998 | Chuter | 606/194 |
| 5,749,852 A | 5/1998 | Schwab et al. | 604/96 |
| 5,752,971 A | 5/1998 | Rosenbluth et al. | 606/192 |
| 5,766,209 A | 6/1998 | Devonec | 604/8 |
| 5,785,641 A | 7/1998 | Davis | 600/30 |
| 5,797,948 A | 8/1998 | Dunham | 606/194 |
| 5,836,951 A | 11/1998 | Rosenbluth et al. | 606/108 |
| 5,855,546 A | 1/1999 | Hastings et al. | 600/3 |
| 5,876,417 A | 3/1999 | Devonec et al. | 606/192 |
| 5,891,386 A | 4/1999 | Deitermann et al. | 264/526 |
| 5,916,195 A | 6/1999 | Eshel et al. | 604/96 |
| 6,004,290 A | 12/1999 | Davis | 604/96 |
| 6,494,879 B2 * | 12/2002 | Lennox et al. | 606/8 |
| 2002/0035391 A1 * | 3/2002 | Mikus et al. | 623/1.11 |
| 2002/0065476 A1 * | 5/2002 | Whalen et al. | 600/587 |
| 2002/0082556 A1 * | 6/2002 | Cioanta et al. | 604/113 |
| 2002/0082610 A1 * | 6/2002 | Cioanta et al. | 606/108 |

FOREIGN PATENT DOCUMENTS

| | | |
|---|---|---|
| EP | 0733379 A1 | 9/1996 |
| EP | 790041 A2 | 8/1997 |
| WO | WO92/18199 | 10/1992 |
| WO | WO93/04727 | 3/1993 |
| WO | WO96/02210 A1 | 6/1995 |
| WO | WO98/00192 | 1/1998 |
| WO | WO 99/59503 | 11/1999 |
| WO | WO00/02503 | 1/2000 |

OTHER PUBLICATIONS

Danilychev et al., "Improving Adhesion Characteristics of Wire Insulation Surfaces," Wire Technology International, vol. 22, No. 2 p. 93–4, 96–7 (Mar.–Apr. 1994), Abstract, WebSPIRS, http://silverp.lib.ncsu.edu:8590/.

Sahagian, R., "Critical Insight: Marking Devices with Radiopaque Coatings," Medical Device & Diagnostic Industry, May, 1999, wysiwyg://12http://www.devicelink.com. (Apr. 9, 2001).

* cited by examiner

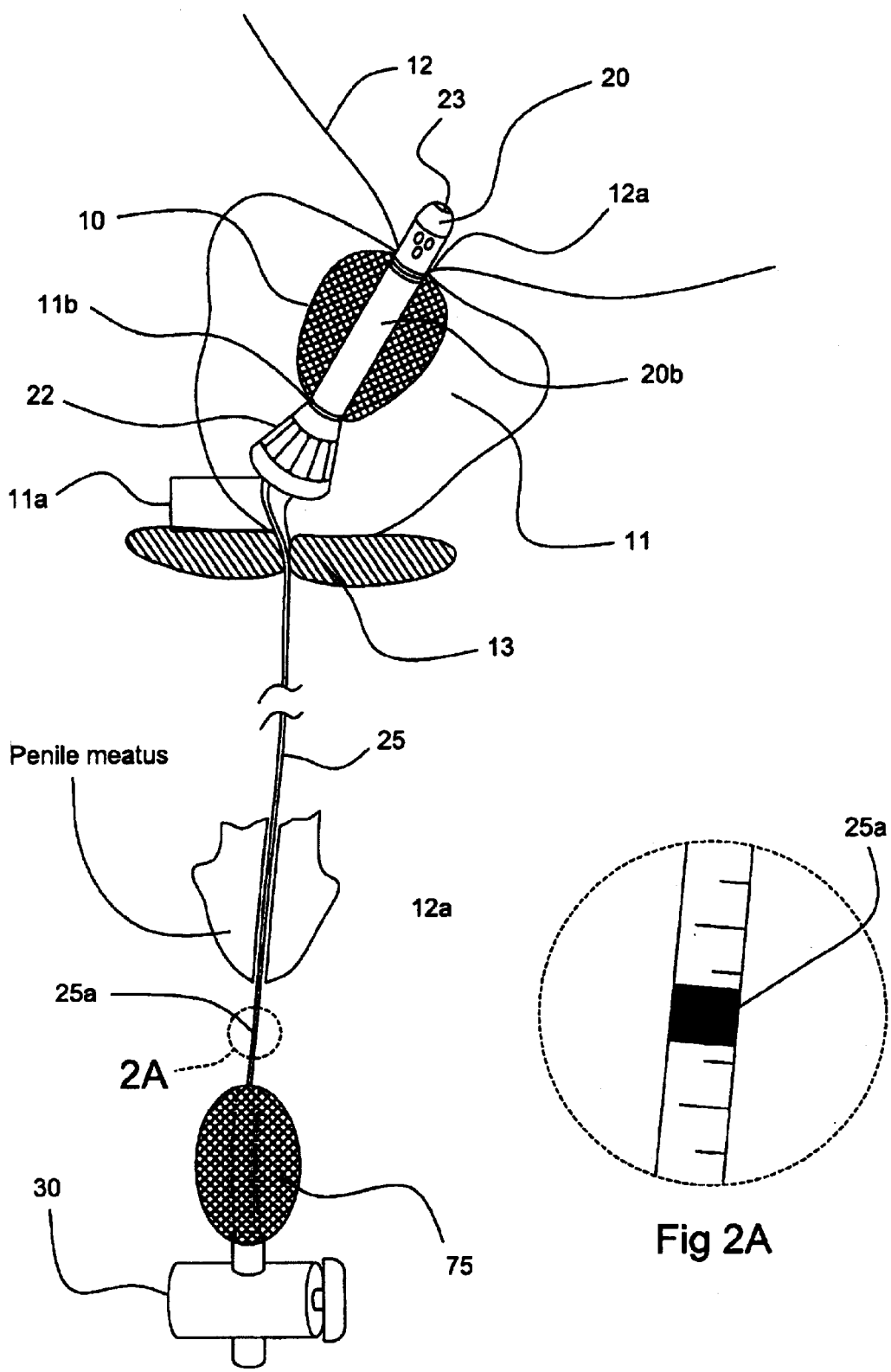

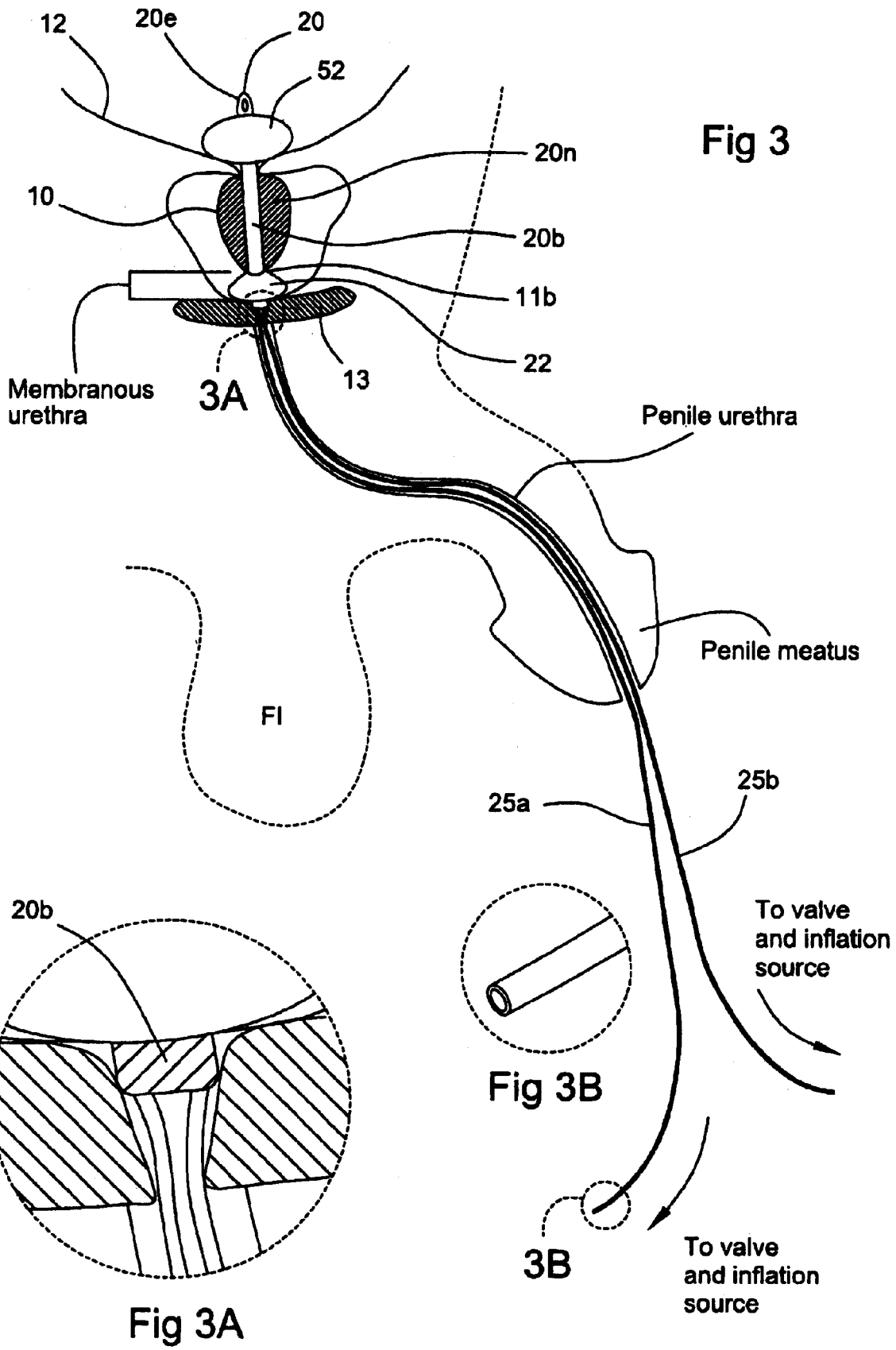

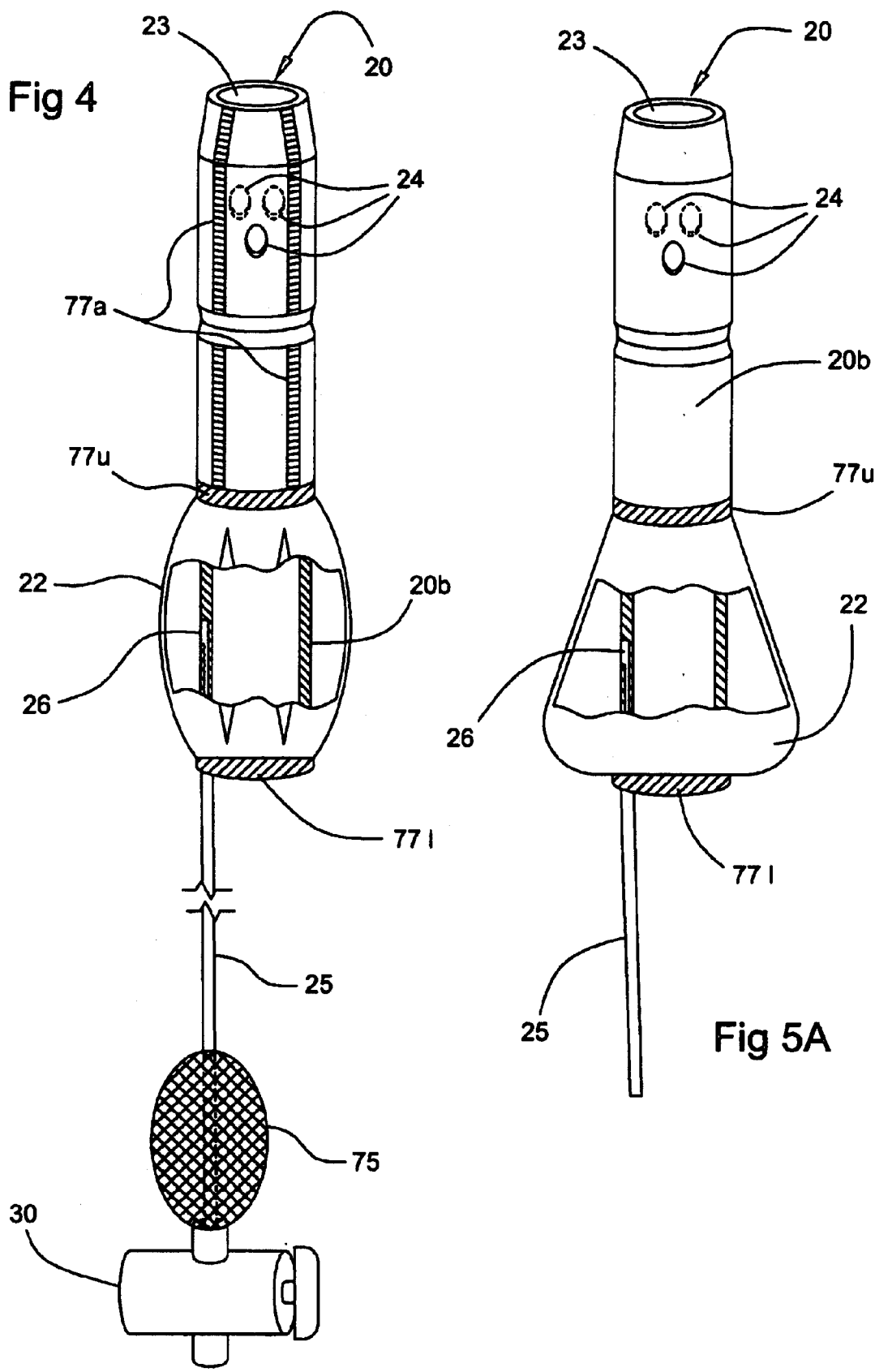

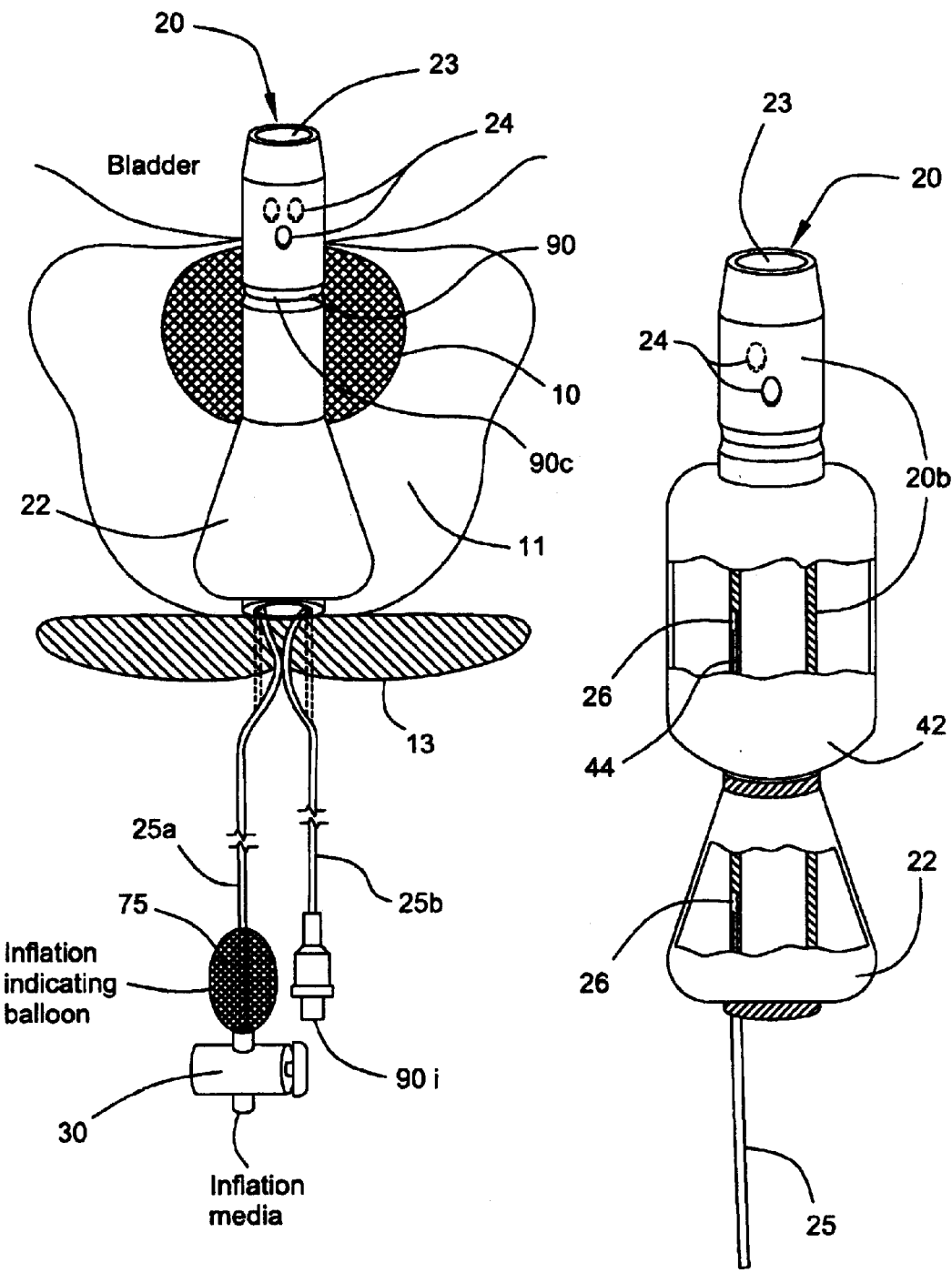

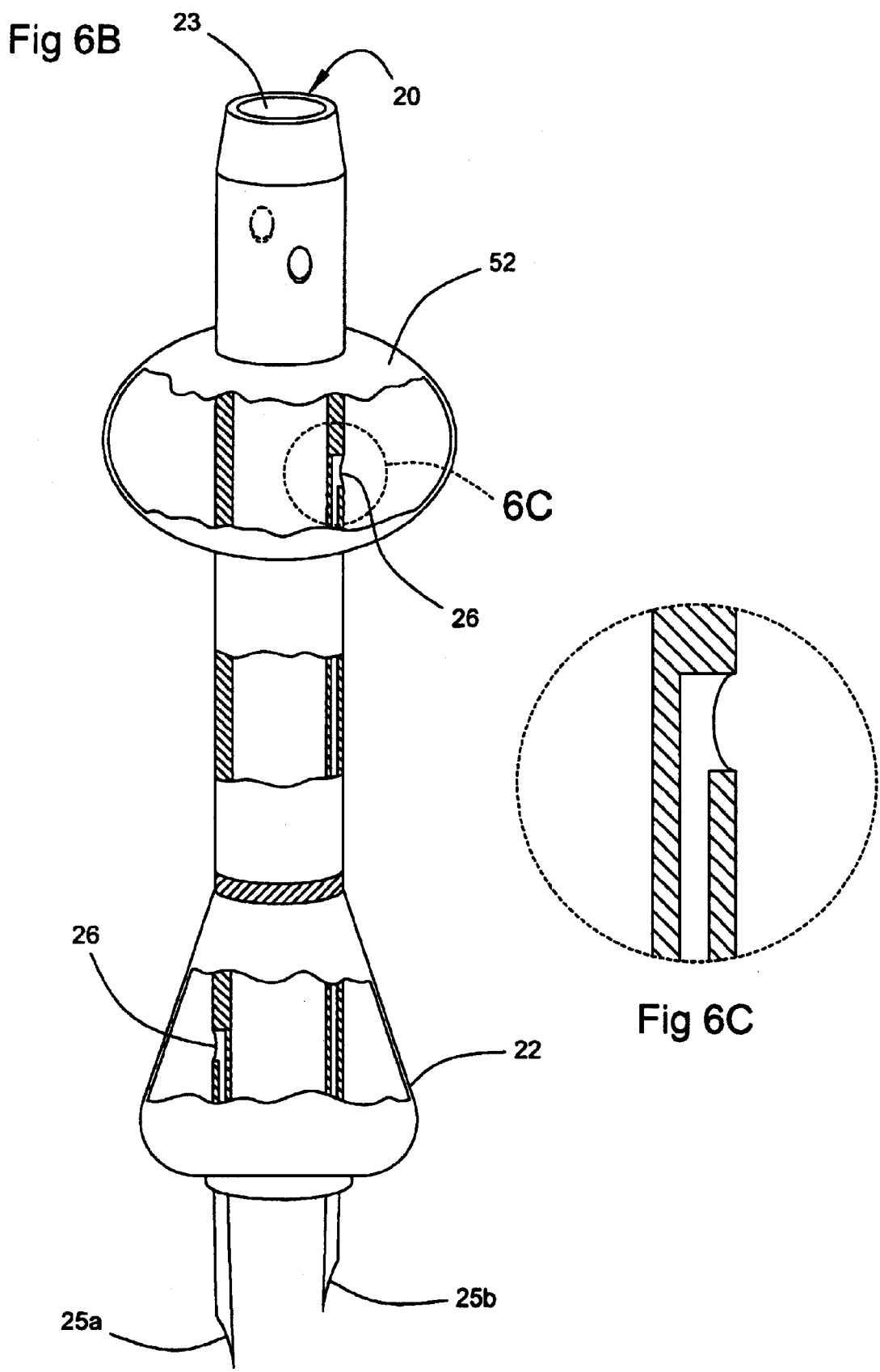

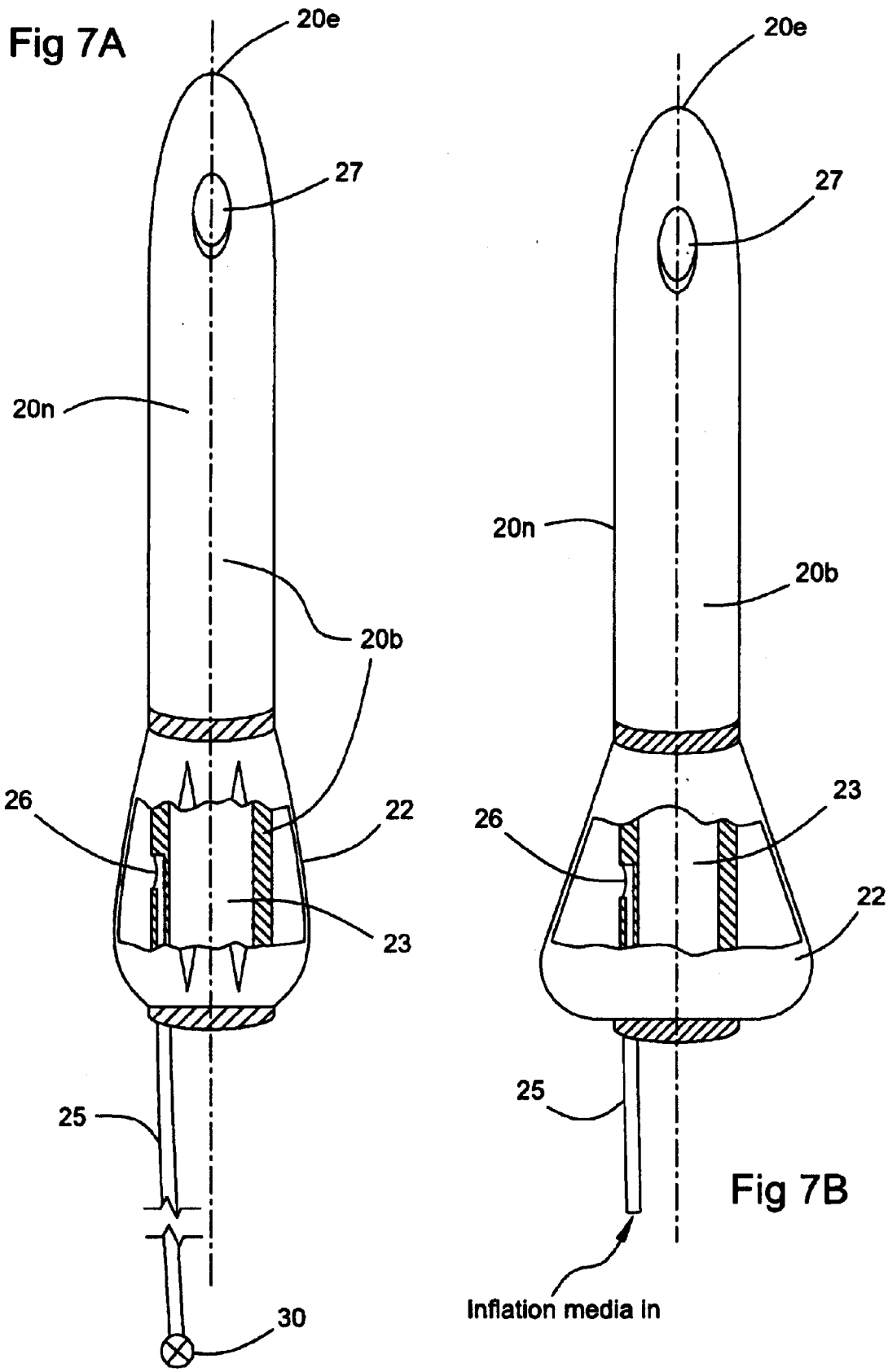

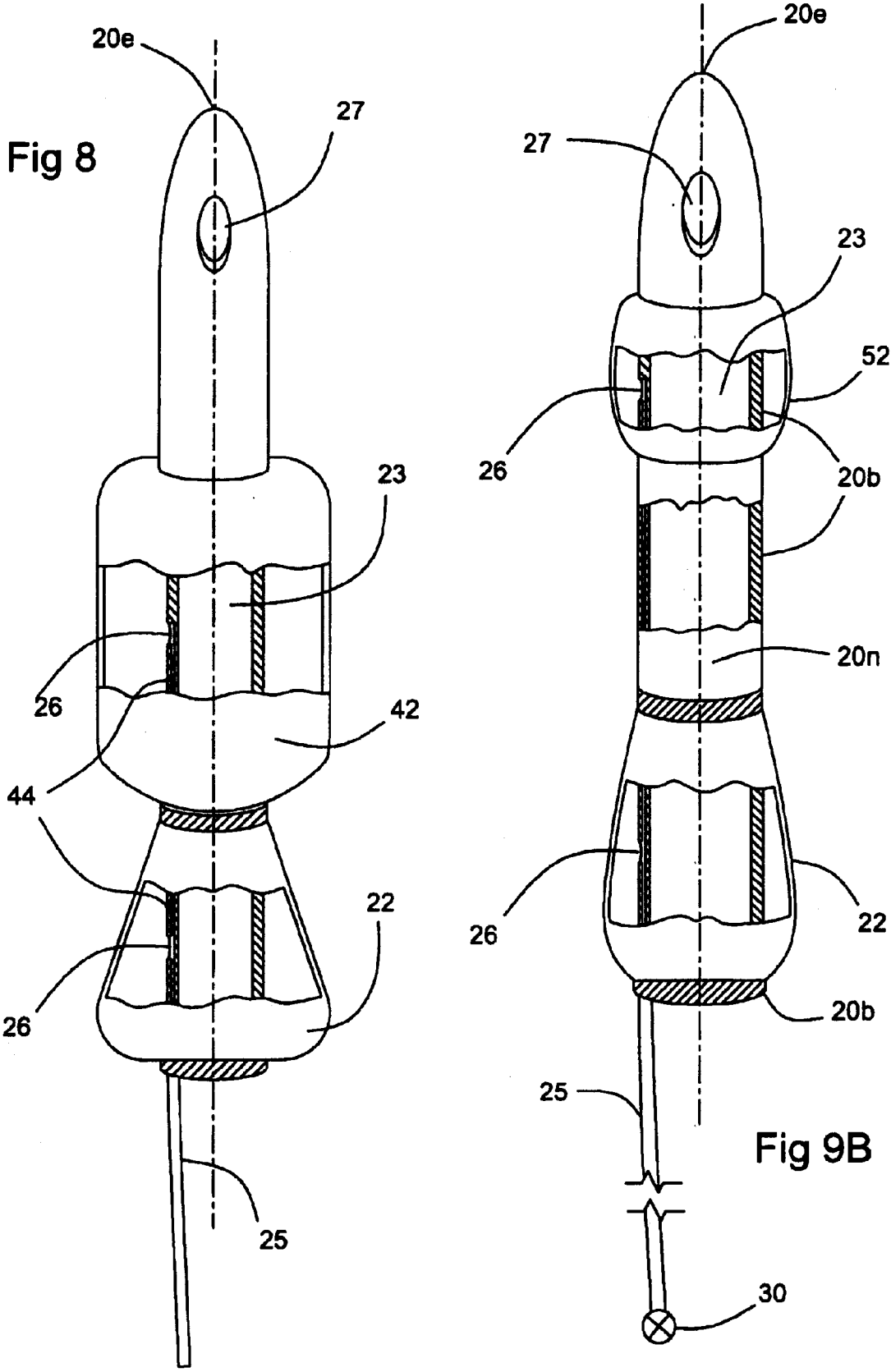

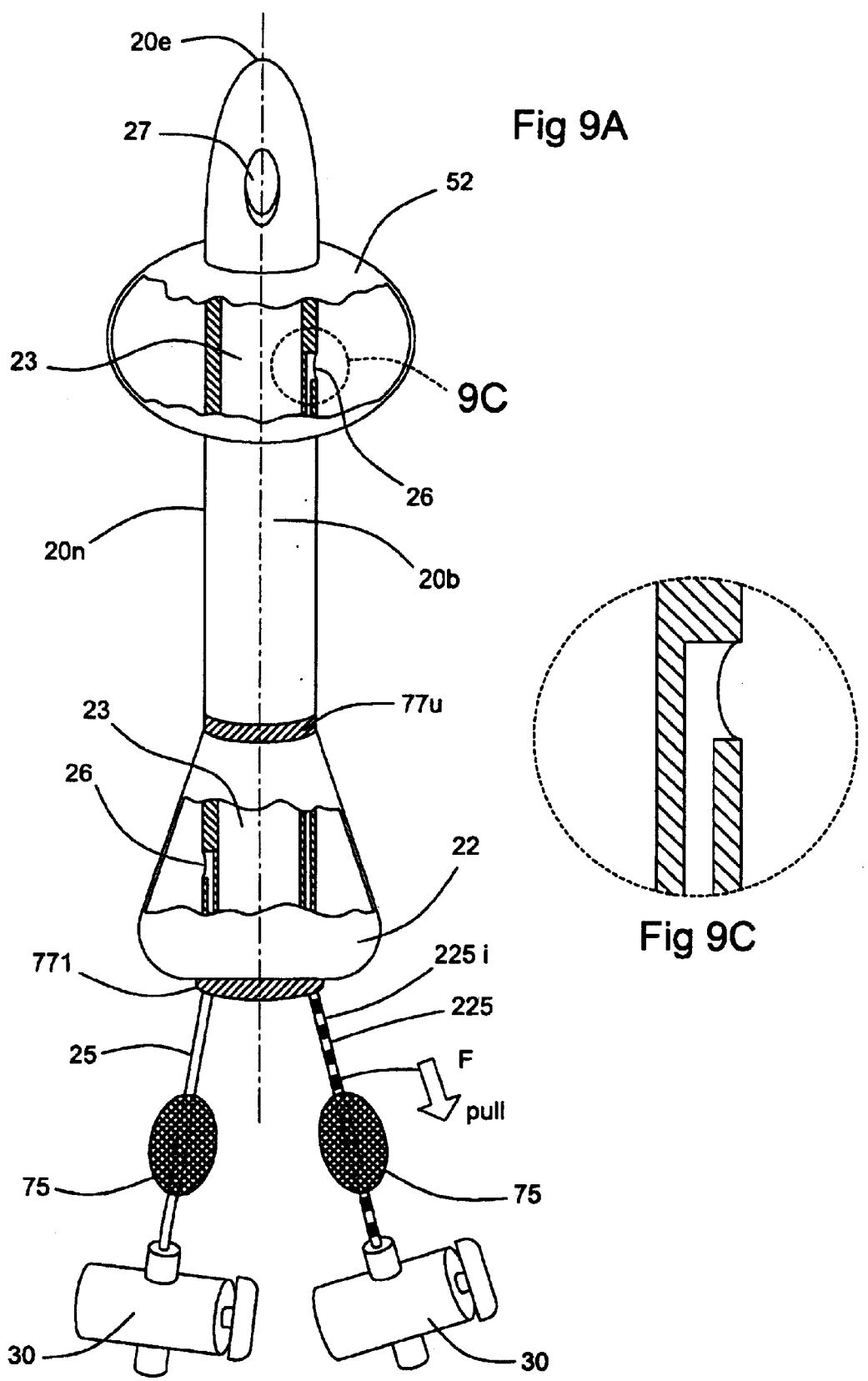

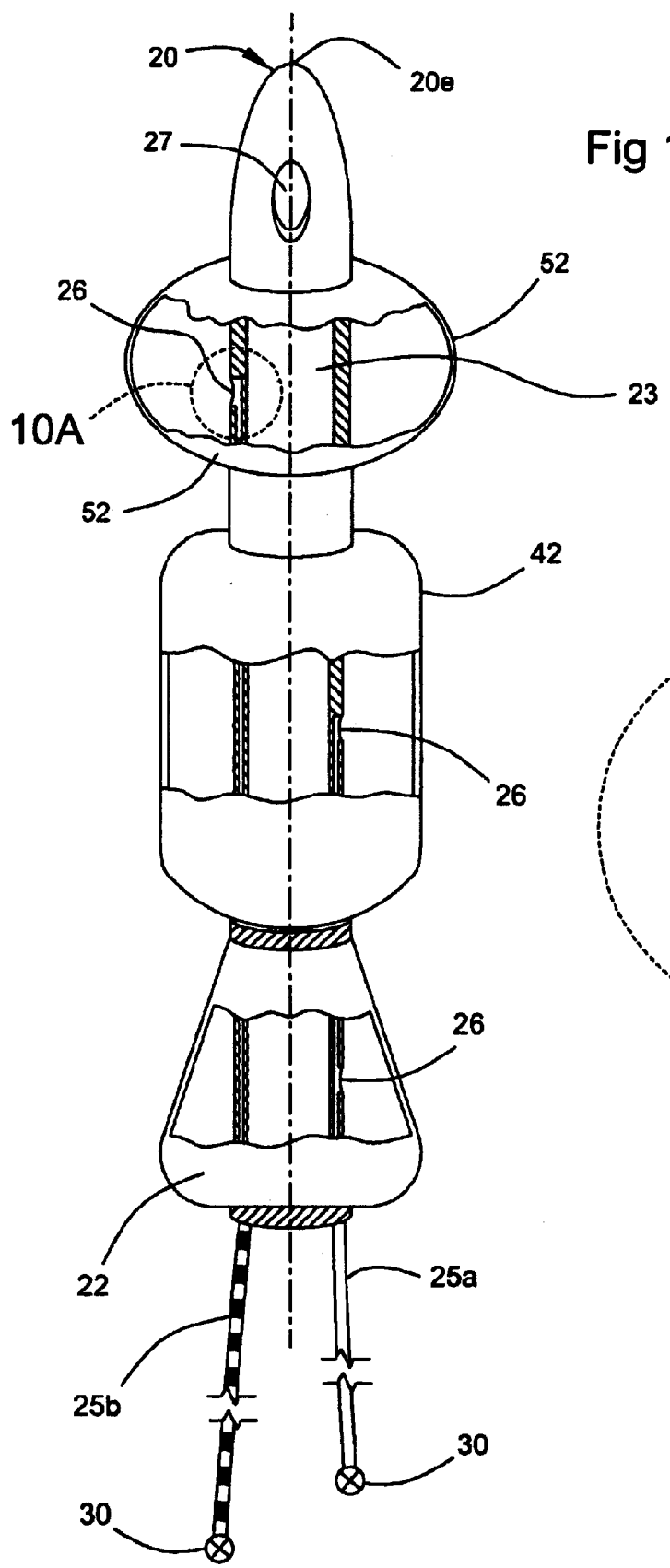

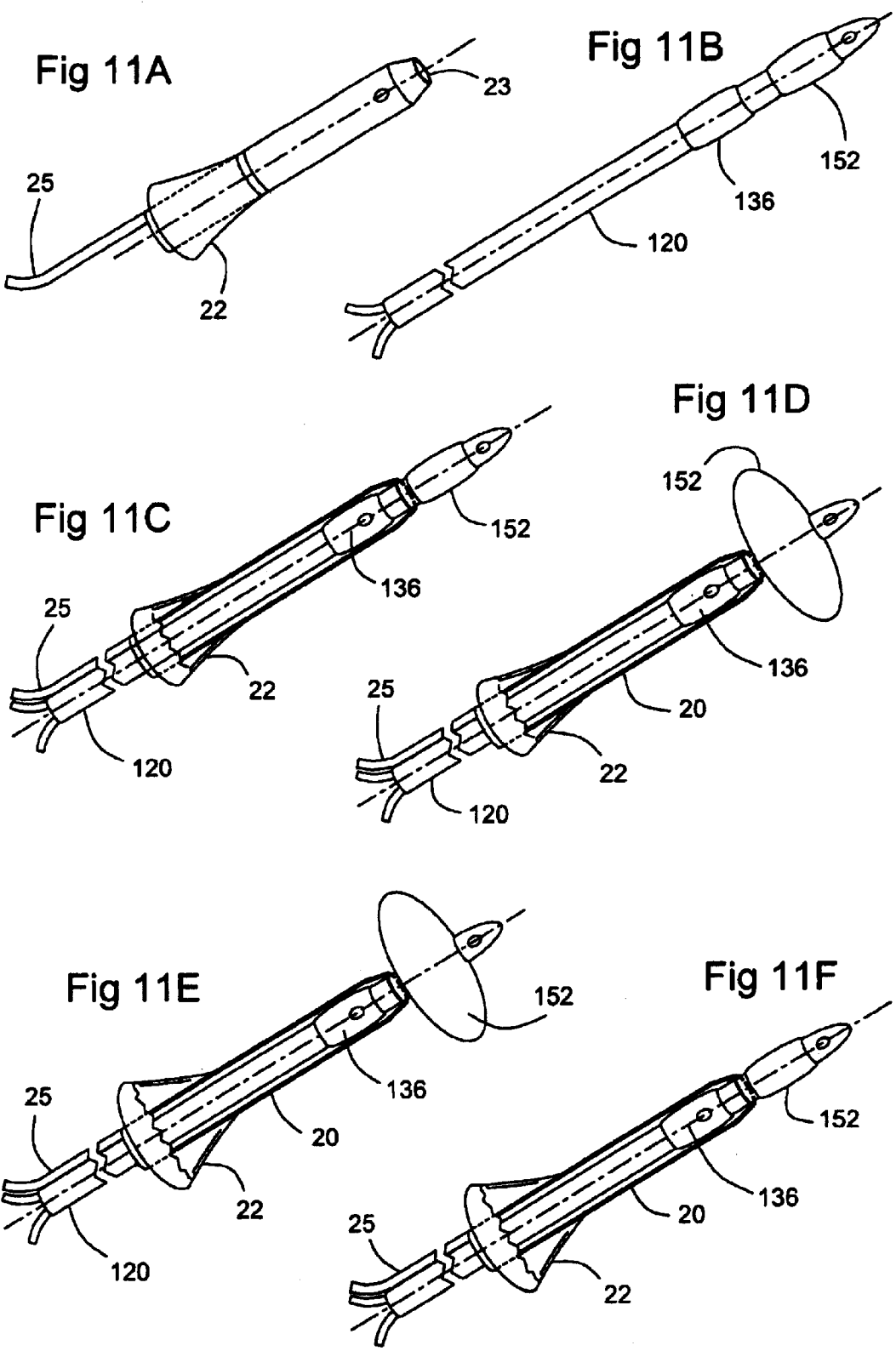

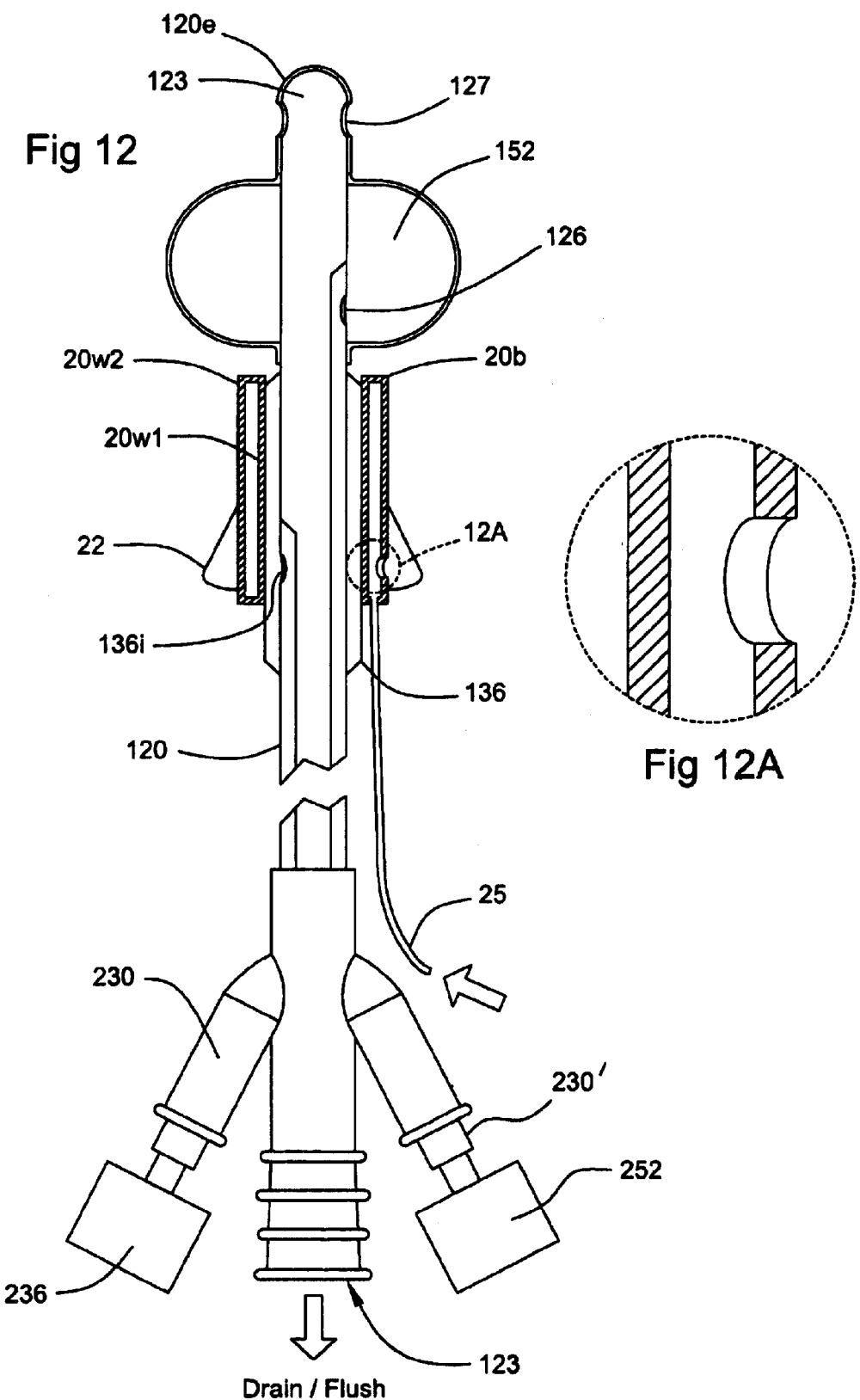

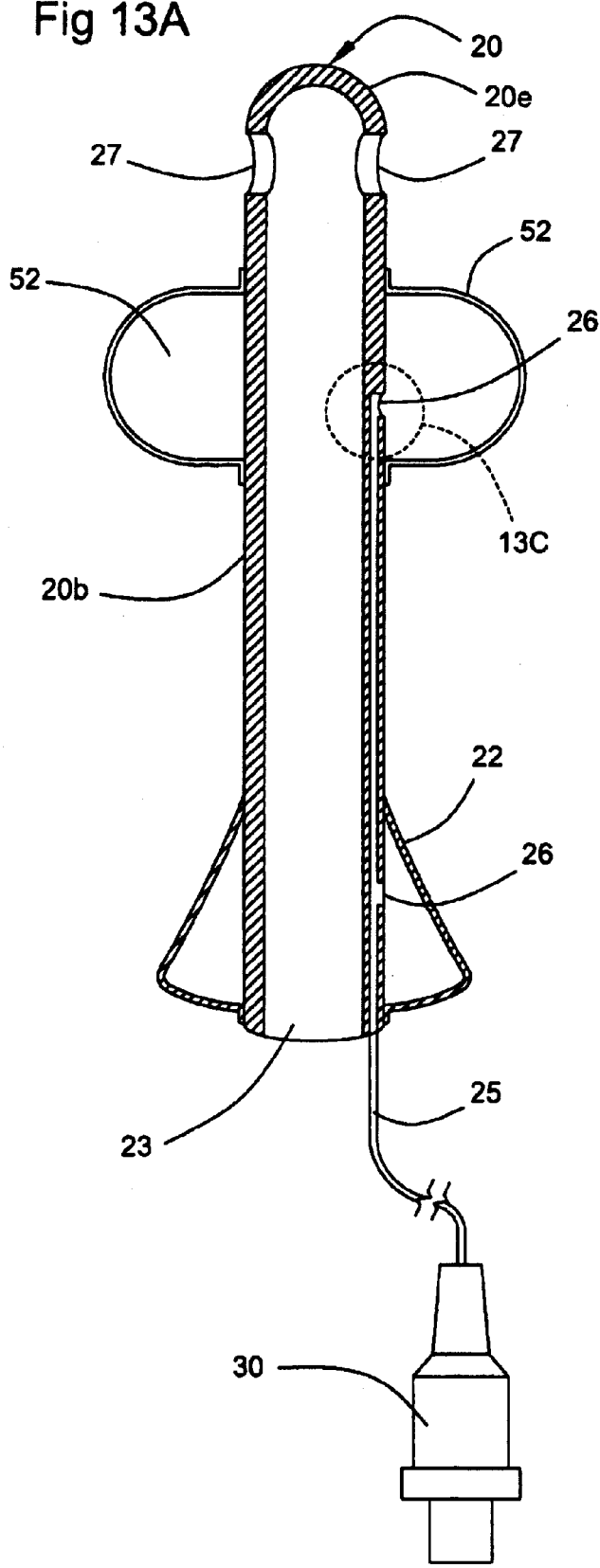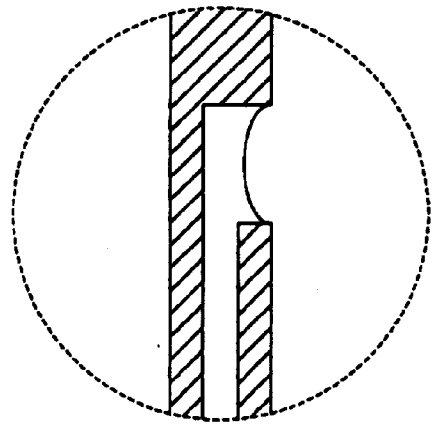
Fig 13A
Fig 13C

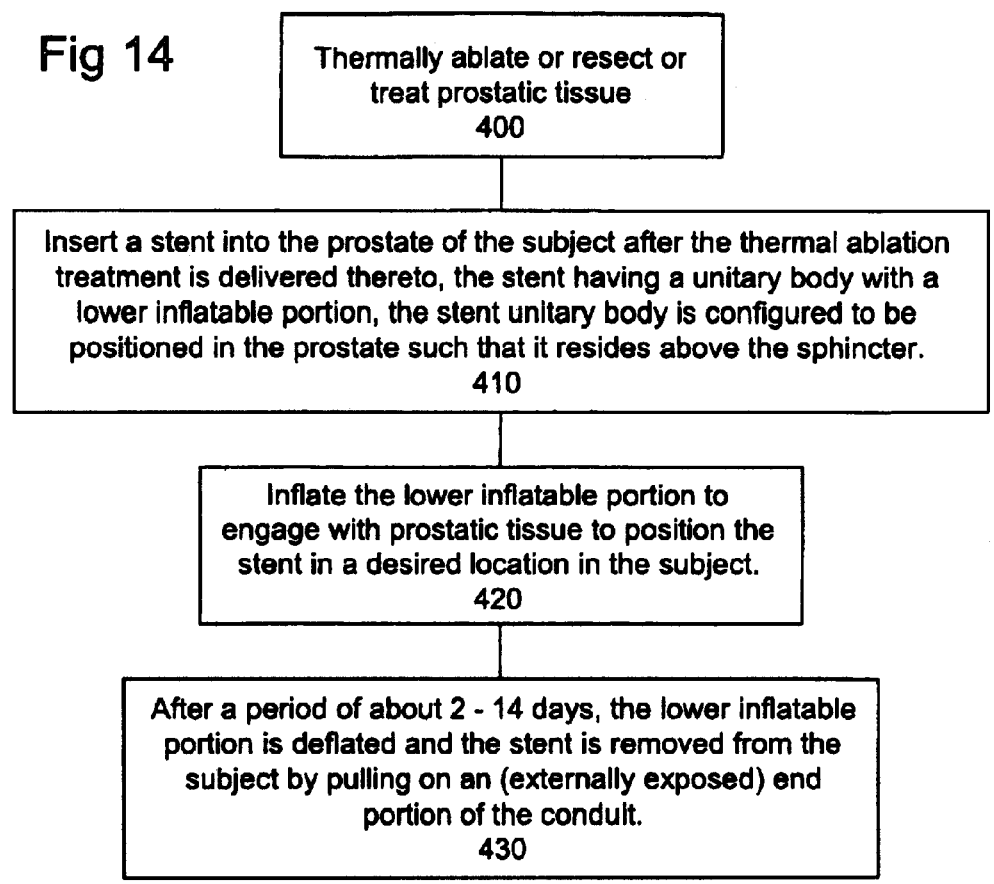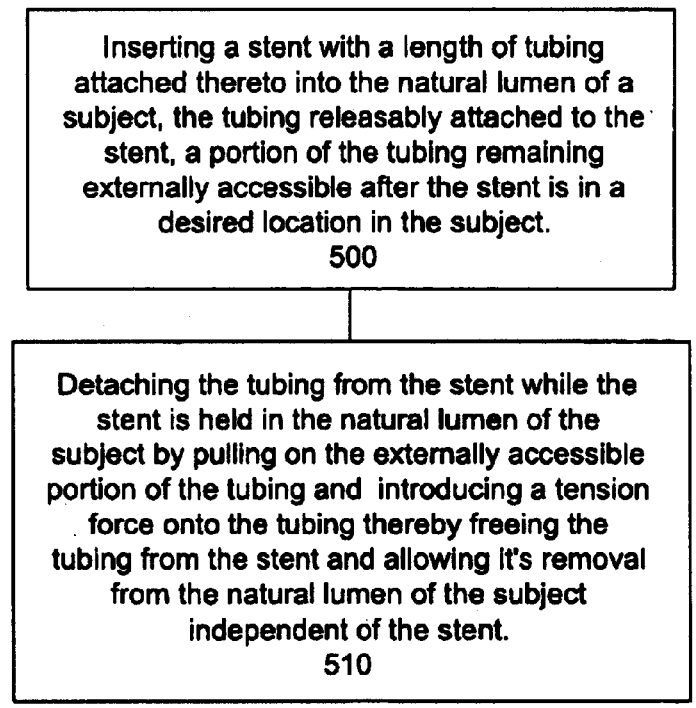

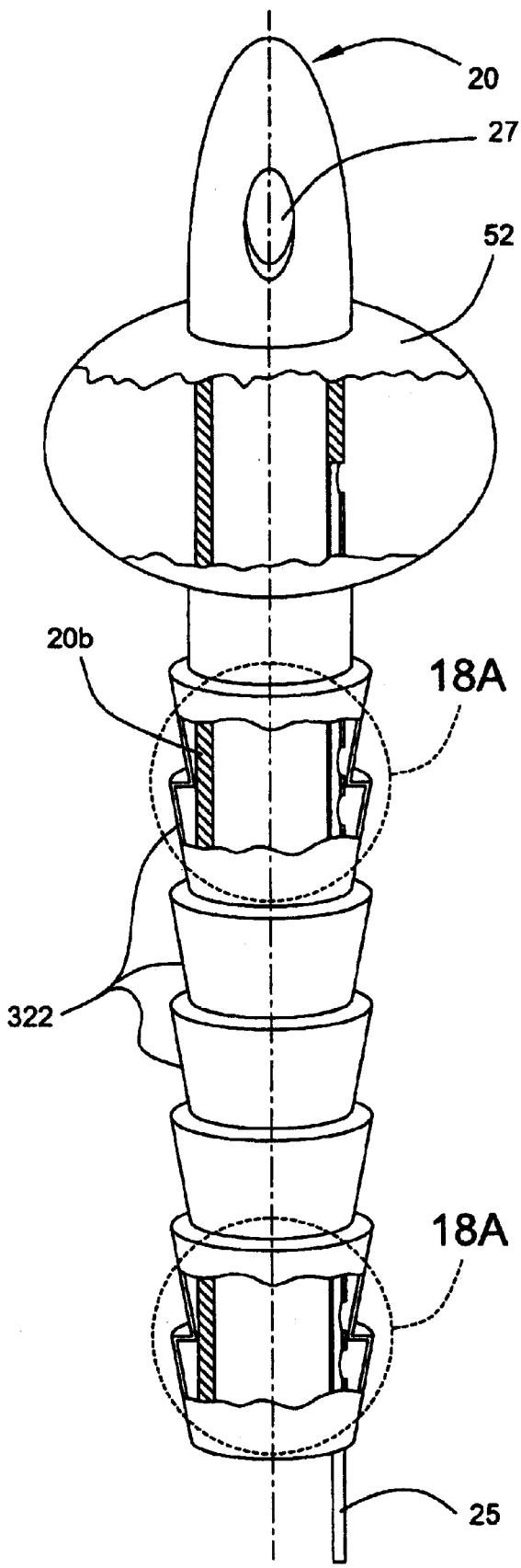
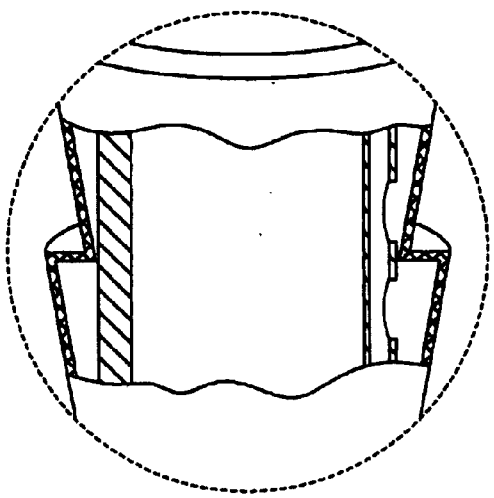
Fig 18
Fig 18A

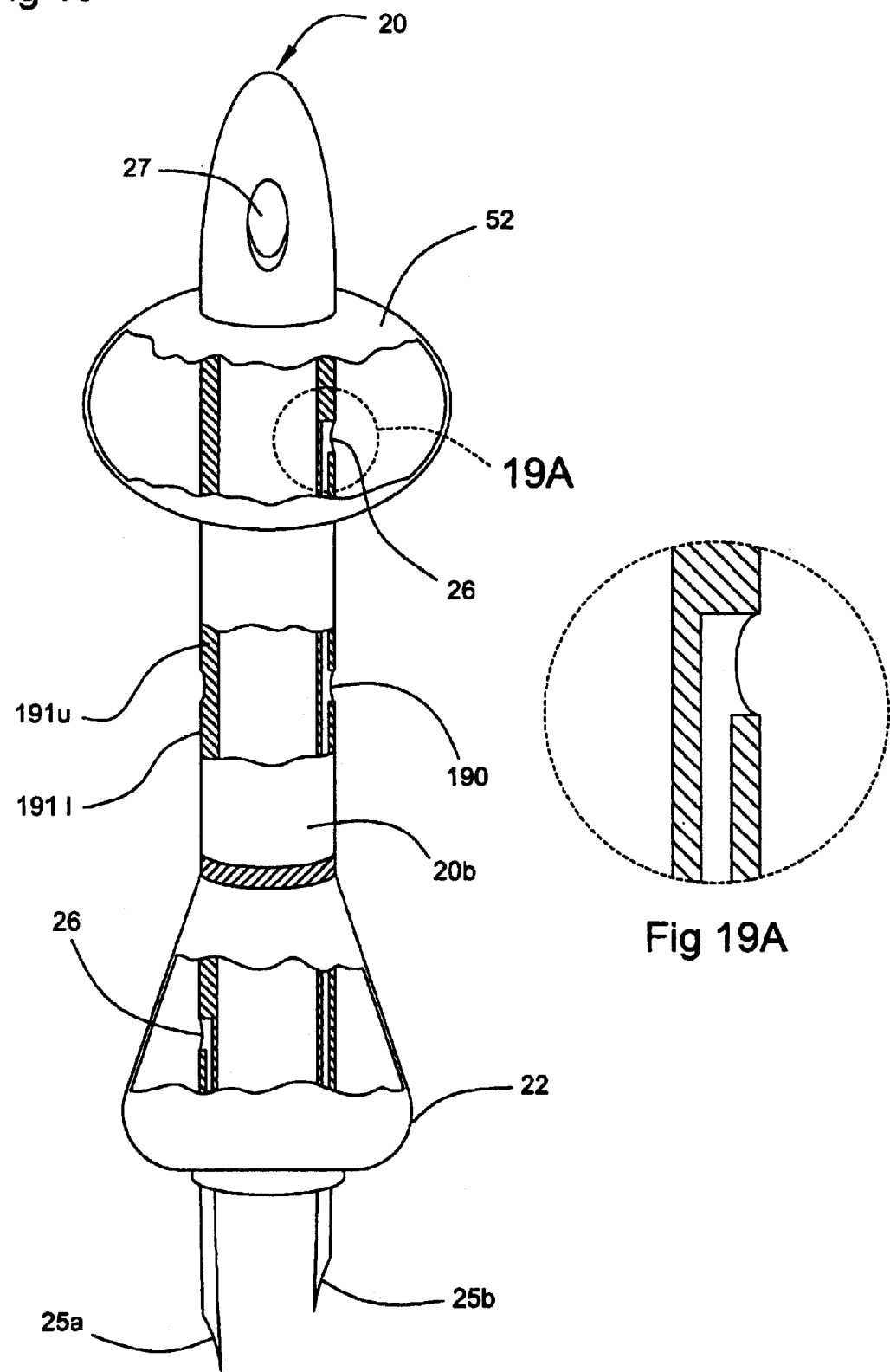

PROSTATIC STENT WITH LOCALIZED TISSUE ENGAGING ANCHORING MEANS AND METHODS FOR INHIBITING OBSTRUCTION OF THE PROSTATIC URETHRA

RELATED APPLICATIONS

This application claims the benefit of priority from U.S. Provisional Application Ser. No. 60/215,156 filed Jun. 30, 2000, the contents of which are hereby incorporated by reference as if recited in full herein.

FIELD OF THE INVENTION

The present invention relates to a stent configured for insertion into a lumen or body cavity of a subject.

BACKGROUND OF THE INVENTION

Conventionally, several types of thermal treatment systems have been proposed to treat certain pathologic conditions of the body by heating or thermally ablating targeted tissue. These thermal treatment systems have used various heating sources to generate the heat necessary to treat or ablate the targeted tissue. For example, laser, microwave, and radio-frequency (RF) energy sources have been proposed to produce the heat which is then directed to the targeted tissue in or around the selected body cavity. Thermal treatment systems have been used to thermally ablate the prostate (as well as other organs, body cavities, and/or natural lumens).

One particularly successful thermal ablation system is directed to thermally ablating the prostate by a thermocoagulation process. This thermal ablation system employs a closed loop liquid or water-induced thermotherapy (WIT) system which heats liquid, typically water, external to the body and then directs the circulating heated water into a treatment catheter which is inserted through the penile meatus and held in position in the subject undergoing treatment to expose localized tissue to ablation temperatures. The treatment catheter includes an upper end portion which, in operation, is anchored against the bladder neck and an inflatable treatment segment which is held relative to the anchored upper end portion such that it resides along the desired treatment region of the prostate. In operation, the treatment segment expands, in response to the captured circulating fluid traveling therethrough, to press against the localized or targeted tissue in the prostate to expose the tissue to increased temperatures associated with the circulating liquid, thereby thermally ablating the tissue at the treatment site. In addition, the pressurized contact can reduce the heat sink effect attributed to blood circulation in the body, thus enhancing the depth penetration of the heat introduced by the inflatable treatment segment into the prostatic tissue.

As an acceptable alternative to surgery (transurethral resection of the prostate (TURP)), the use of WIT (water-induced thermotherapy) has been shown to be particularly suitable for the treatment of BPH (benign prostatic hyperplasia). Generally stated, the term "BPH" refers to a condition wherein the prostate gland enlarges and the prostatic tissue increases in density which can, unfortunately, tend to close off the urinary drainage path. This condition typically occurs in men as they age due to the physiological changes of the prostatic tissue (and bladder muscles) over time. To enlarge the opening in the prostatic urethra (without requiring surgical incision and removal of tissue), the circulating hot water is directed through the treatment catheter, which is inserted into the penile meatus up through the penile urethra and into the prostate as described above. The treatment segment expands with the hot water held therein to press the inflated treatment segment against the prostate, which then conductively heats and thermally ablates the prostatic tissue. The circulating water is typically heated to a temperature of about 60–62° C. and the targeted tissue is thermally treated for a period of about 45 minutes to locally kill the tissue proximate the urinary drainage passage in the prostate and thereby enlarge the urinary passage through the prostate.

Subsequent to the delivery of the thermal ablation treatment, the treated tissue in the prostate undergoes a healing process. Initially, the ablated tissue can expand or swell due to inflammation or edema which can undesirably block or obstruct the prostatic urethra. Further, during the healing period, portions of the treated tissue can slough off and create an undesirable and unduly limited opening size. This post-ablation treatment opening size can be positively influenced by "molding" the ablated tissue during the healing cycle to contour the tissue about a catheter or stent held thereat. Therefore, to facilitate proper healing and to enhance the efficacy of the ablation therapy, either the treatment catheter is left in the subject for a period of time and/or a post treatment catheter, such as a conventional Foley catheter, is positioned in the subject. However, the amount of time that the treatment or post-treatment catheter must reside in the subject can be from 2–14 days, or even longer. Therefore, it is desirable to configure the post-treatment catheter in a minimally invasive manner to allow normal operation of the sphincter, remove the need for the use of an incontinence bag, and reduce the inconvenience or discomfort to the user.

Conventionally, Foley-type catheters with bladder anchoring balloons located on an upper end portion have been used as post-treatment catheters to allow the thermally ablated tissue to mold around the catheter perimeter during the initial healing phase. While these type catheters allow the post-treatment catheter to be securely positioned relative to the bladder neck of the subject, natural operation of the sphincter is inhibited, and the configuration is relatively cumbersome (in position it extends through the penile urethra) and can be considered unduly invasive by the user and may increase the risk of urinary tract infection (UTI) when in position in the subject (particularly, when used for extended periods of time). Other post-treatment catheter configurations (also known as "indwelling catheters" and "stents") have also been proposed; however, some of the catheter types can inhibit the ability to flush out blood clots which may exist from the therapy, and others are undesirably invasive to the user and/or prevent or inhibit the natural operation of the sphincter. Still others are not able to be properly located within the prostatic cavity about the treatment region and/or are unable to retain their desired position in the prostate over time. Still others can, during prolonged use, promote muscle atrophy and/or localized tissue necrosis.

Examples of known post-treatment catheters or stents are described in U.S. Pat. No. 5,916,195 to Eshel et al., U.S. Pat. Nos. 5,876,417 and 5,766,209 to Devonec et al., and U.S. Pat. No. 3,811,450 to Lord. However, there remains a need to provide improved and/or minimally invasive post-treatment catheters or stents which are cost effective and can be positioned and located in the prostate proximate the treated tissue during the post thermal ablation process or healing cycle (which can contour or mold the tissue) and which can be easily removed at the appropriate time.

OBJECTS AND SUMMARY OF THE INVENTION

It is therefore an object of the present invention to provide a stent which is suitable for inhibiting post thermal ablation obstruction in the prostate and which is configured in a minimally invasive manner to the wearer.

It is another object of the present invention to provide a stent which can be inserted through the penile meatus and penile urethra to be positioned in the prostatic urethra and held in a desired position relative to the thermally treated tissue during prolonged use.

It is yet another object of the present invention to provide a stent which can be locally anchored in a relatively stable manner in the prostate such that longitudinal migration or movement toward or away from the bladder is inhibited.

It is another object of the present invention to provide a device which can inhibit obstruction in the prostatic urethra to keep the urinary drainage path open such that the subject is able to discharge urine in a normal manner.

It is an additional object of the present invention to provide a way to monitor the movement of catheters and/or to provide improved ways to determine that the integrity of the inflation system is intact.

It is another object of the present invention to provide improved stents which are able to inhibit obstruction in a lumen or cavity.

These and other objects are satisfied by the present invention which provides, inter alia, minimally invasive unitary body stents having a length of elongated small tubing which extends therefrom. The length of the small tubing or conduit is sufficient such that it can extend from the unitary body and along the penile urethra to a position outside the body. The stents are configured to reside above the sphincter such that they are held in the prostate during a healing period. Similarly, the present invention includes methods of treating BPH (and other prostate conditions) to inhibit obstruction in the prostatic urethra during a healing period after a thermal ablation treatment therapy.

More particularly, a first aspect of the present invention is a prostatic stent configured for insertion into the male urethra of a subject. The male urethra generally includes, in serial order from the externalmost portion to the internal portion, the penile meatus, the penile urethra, the bulbous urethra, the sphincter, the membranous urethra, the prostatic urethra, the bladder neck and the bladder. The prostatic stent includes a unitary tubular body having a central lumen extending therethrough and a first cross-sectional width thereacross. The stent also includes a tissue-engaging inflatable balloon positioned on a lower perimeter portion of the unitary body and at least one conduit having opposing upper and lower end portions with a fluid lumen formed therein. A portion of the upper end of the conduit is attached to the unitary tubular body such that it is in fluid communication with the inflatable balloon. The conduit has a second cross-sectional width which is less (preferably substantially less) than the first cross-sectional width of the unitary tubular body. In position in the subject, the stent is configured such that the unitary body resides above the sphincter and the conduit extends through the sphincter and out of the penile meatus of the subject. In addition, the conduit is configured in size and/or cross section such that it allows substantially natural closing of the sphincter when the stent is in position in the subject.

Another aspect of the present invention is a set of prostatic stents, each configured for insertion into the male urethra of a subject as stated above. However, the set is provided such that each unitary body is sized a different length to allow customized fit to a particular subject (the portion of the stent body which is adapted to reside in the membranous and prostatic urethra itself and typically ranges in length from about 4–10 cm).

Yet another aspect of the present invention is a method of treating BPH. The method includes the steps of (a) thermally ablating a localized treatment region in the prostatic urethra of a subject such that the urethra below the prostatic urethra, about or proximate the membranous urethra, remains substantially non-ablated; (b) inserting a stent into the prostate of the subject after the thermally ablating step, the stent having a unitary body, a lower inflatable portion formed thereon, and a conduit extending downwardly therefrom; (c) positioning the stent in the subject such that the unitary body resides above the sphincter and the conduit extends downwardly therefrom through the sphincter and out of the penile meatus, wherein the conduit is sized to allow the sphincter to function substantially normally with the stent in position in the body; (d) inflating the lower inflatable portion after the inserting step such that the lower inflatable portion engages with tissue which is located below the treatment region and a portion of the stent resides proximate the treatment region and above the sphincter; (e) inhibiting the obstruction or closure of the prostatic urethra during a healing period subsequent to said thermal ablating step; (f) deflating the lower inflatable portion; (g) and removing the stent after the deflating step and after a period of about two to fourteen days from the time of initial insertion of the stent.

In certain embodiments, the stent is removed by deflating the lower inflatable portion and then pulling the conduit to force the stent from the subject. The inserting step may be carried out after an initial healing period of about 12–72 hours (typically when a treatment catheter is left in the body), and preferably, about 24–48 hours, from the end of the thermal ablation therapy to avoid unnecessary contact or manipulation of the treatment site to inhibit bleeding of the treated tissue. Inserting the stent after an initial healing period can reduce bleeding which may occur upon premature removal of the treatment catheter after delivery of the active thermal ablation treatment.

Another aspect of the present invention is a method of inhibiting the obstruction of the prostatic urethra in a minimally invasive manner, comprising the step of inserting a stent, having a unitary body and a length of at least one conduit attached thereto, into the penile meatus of a subject and along the penile urethra until the stent is located in a desired location in the prostatic urethra such that the stent unitary body resides above the sphincter and the conduit extends through the spinchter and out of the penile meatus, wherein the conduit is sized to allow the sphincter to close in a substantially natural manner when the stent is in position in the subject.

The at least one conduit can be two (or more) conduits: a first conduit in fluid communication with a bladder anchoring balloon, and a second conduit in fluid communication with a lower inflatable portion. In addition, the first conduit can be releasably attached to the stent. In one embodiment, one conduit can be detached from the stent while the stent is in situ (in the subject) after the step of positioning the stent into the subject's prostate, when the detachable conduits in fluid communication with the anchoring balloon inflated after the positioning step.

In other embodiments, the conduit can include externally visible indicia of movement positioned along an externally disposed portion of the conduit (when the stent is in the subject). The method can, thus, include the step of monitoring the movement of the stent in the subject corresponding to the change in position of the external indicia. In addition externally visible indicia of the integrity of, or proper degree of inflation of, the inflation balloons in the body (whether localized or bladder anchoring balloons) can be operably associated with the conduit(s). The stent can also be configured with radiopaque markers to allow for positional verification of the stent (such as by X-ray) when in the body. In addition, the external surface of the stent, particularly the unitary body and inflation portions, can include surface treatments such as anti-microbial and/or anti-frictional coatings.

Yet another aspect of the present invention is a further method of treating BPH. The method comprises the steps of (a) inserting a treatment catheter configured to circulate heated liquid along the penile urethra to the prostate of a subject; (b) circulating liquid heated to above about 45° C. in the treatment catheter; (c) directing the circulating heated liquid of the circulating step such that it travels, captured in the treatment catheter, to a localized treatment region in the prostate; (d) exposing targeted tissue in the prostate in a localized treatment region to a temperature of above about 45° C. for a predetermined thermal ablation treatment period corresponding to liquid provided by the circulating and directing steps; (e) terminating the circulation of the heated liquid after the thermal ablation treatment period; (f) leaving the treatment catheter in the subject after the terminating step for an initial healing period of from about 12–72 hours; (g) removing the treatment catheter after the initial healing period; (h) inserting a post-treatment stent having a unitary body and at least one conduit extending therefrom into the subject after the removing step; (i) positioning the post-treatment stent with a unitary body and a elongated conduit extending therefrom in the subject such that the unitary body resides above the sphincter and the conduit extends through the sphincter, the penile urethra, and the penile meatus such that a lower portion resides outside the subject, and such that a portion of the stent resides in the localized treatment region of the prostate to allow the tissue to mold thereabout during a post thermal ablation healing period, wherein the post-treatment stent comprises a lower inflatable portion; (j) expanding the lower inflatable segment such that it engages with tissue below the localized treatment region and above the sphincter; and (k) removing the stent from the subject, after deflating the lower inflatable segment, by pulling on the conduit located outside the subject to dislodge and slide the stent along the penile urethra to free the stent after a healing period of about 2–14 days thereby inhibiting the obstruction of the prostatic urethra by allowing the tissue to mold or migrate about the perimeter of the stent as it heals to facilitate a desired prostatic urethra opening thereabout.

In a preferred embodiment, the conduit includes graduation marks on the portion which is adapted to be external of the subject when the stent is in position in the subject, and the method further comprises the step of monitoring the movement of the stent in the body corresponding to the travel of the graduation marks toward or away from the penile meatus. In another embodiment, the at least one conduit comprises two conduits both attached to the unitary body of the stent, and the method further comprises the steps of detaching a selected one of the conduits in situ from the stent body and removing it from the subject when the stent is in use (and in position in the body). As noted above, the stent can also include externally visible movement indicia and inflation indicia.

Advantageously, the present invention provides post-treatment stents or stents which can be used to inhibit prostate obstruction in the urinary drainage path in a minimally invasive manner. The unitary body stent is configured to reside in the subject above the sphincter with only one or more conduits extending therefrom and out of the body of the subject. The stent can include one or more of a lower tissue engaging anchoring balloon, an upper bladder neck anchoring balloon, and an expandable tissue molding intermediate section. The conduits can be configured to direct an inflation medium to and from the desired inflation region in the stent. One or more of the conduits can be releasably attached to the stent such that it is detachable in situ. The detachable conduit can be externally visually marked or configured such that it is readily identifiable during operational use by a clinician.

The conduit can also include external indicia of movement (and/or a "stop"), such as graduation marks to allow a user or clinician to monitor the movement of the catheter toward or away from the penile meatus or other landmark to identify when or if the stent has dislodged from its desired location in the subject.

The unitary body stent is configured to allow drainage and/or flushing liquids to be directed into the subject therethrough, and is particularly suitable for chronic wearing (such as 2–14 days) by a user undergoing a healing period after a thermal ablation therapy has been applied to a localized region of the prostate. The instant invention is also particularly suitable for insertion after an initial healing period to reduce irritation introduced to the ablated tissue (which can reduce the number of blood clots produced by the subject). The stent can include one or more conduits, one of which can be used to deliver medicaments or saline rinses to the treatment region during the healing process (to promote healing and/or inhibit UTI). The stent can be positioned in the body by attachment to a pusher which is configured to securely hold the stent thereagainst by inflation of one or more attachment balloons.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 2 is a schematic illustration of the prostatic portion of the male urethra illustrating a stent in position in the subject after thermal ablation treatment and configured according to embodiments of the present invention.

FIG. 2A is an enlarged view of a region of the stent shown in FIG. 2.

FIG. 3 is a schematic illustration of the prostatic portion of the male urethra illustrating an alternate embodiment of a stent in position according to embodiments of the present invention.

FIGS. 3A and 3B are enlarged views of a region of the stent illustrated in FIG. 3.

FIG. 4 is a front partial cutaway view of a stent similar to that shown in FIG. 2 illustrating the tissue anchoring balloon in a deflated configuration.

FIG. 5A is a front partial cutaway view of the stent shown in FIG. 4 illustrating the tissue-anchoring balloon inflated to an enlarged shape according to embodiments of the present invention.

FIG. 5B is a front view of an alternate embodiment of a stent similar to that shown in FIG. 5A illustrating the use of two conduits, one for inflating the anchoring balloon, and one for delivering medicaments, drugs, or rinses to the targeted (ablated prostatic tissue) while the stent is in position in the body according to embodiments of the present invention.

FIG. 6A is a front partial cutaway view of another embodiment of a stent similar to that shown in FIGS. 2–5A, and 5B, but including an inflatable tissue molding intermediate portion.

FIG. 6B is a front partial cutaway view of an additional embodiment of a stent similar to that shown in FIGS. 2–5A, and 5B but including a bladder (or distal) anchoring balloon.

FIG. 6C is an enlarged view of a region of the stent shown in FIG. 6B.

FIG. 7A is a front partial cutaway view of an alternate embodiment of a stent according to embodiments of the present invention.

FIG. 7B is a front partial cutaway view of the stent shown in FIG. 7A illustrating the lower anchoring balloon inflated to a ramped shape.

FIG. 8 is a front partial cutaway view of an additional embodiment of the present invention, illustrating a similar stent to that shown in FIGS. 7A and 7B with an intermediate tissue molding inflatable portion.

FIG. 9A is a front partial cutaway view of yet another embodiment of a stent according to embodiments of the present invention, illustrating a unitary body stent with both a bladder neck and tissue-anchoring balloon in the inflated position.

FIG. 9B is a front partial cutaway view of the stent shown in FIG. 9A showing the stent with only a single inflation conduit and the tissue and bladder neck anchoring balloons in the deflated state according to embodiments of the present invention.

FIG. 9C is an enlarged view of a region of the stent shown in FIG. 9A.

FIG. 10 is a front partial cutaway view of another embodiment of a stent according to the present invention.

FIG. 10A is an enlarged view of a region of the stent shown in FIG. 10.

FIGS. 11A–11F are a sequential series of figures which illustrate an operational sequence according to embodiments of the present invention. FIG. 11A is a side view of a stent similar to that shown in FIGS. 2–5.

FIG. 11B is a side view of a pusher configured to be positioned inside of the stent to help position the stent in the body of the subject.

FIG. 11C is a side partial cutaway view of the stent shown in FIG. 11A and the pusher shown in FIG. 11B, showing the tissue anchoring balloon in a deflated state and with the pusher insertion guide being inserted to and a portion of the pusher being inflatably transversely expanded to affix to the central lumen of the stent in preparation for guiding the stent through the penile meatus into the desired location in the prostate (or into other desired cavities or lumens) according to embodiments of the present invention.

FIG. 11D is a side partial cutaway view of the stent and guide shown in FIG. 11C. This figure illustrates an anchoring balloon (on the pusher) inflated.

FIG. 11E is a side partial cutaway view of the stent and pusher shown in FIG. 11D which illustrates the stent anchoring balloon inflated after the guide-positioning balloon has been inflated and the desired position obtained.

FIG. 11F is a side partial cutaway view of the stent and pusher shown in FIG. 11E, illustrating the pusher or insertion guide fixation balloon deflated so the pusher can be removed from the stent, leaving the stent in position in the body.

FIG. 12 is a side enlarged partial section view of an alternate embodiment of a pusher or insertion guide and stent according to embodiments of the present invention.

FIG. 12A is an enlarged view of a region shown in FIG. 12.

FIG. 13A is an enlarged side section view of a stent similar to that shown in FIGS. 9A and 9B.

FIG. 13C is an enlarged view of a region of the stent shown in FIG. 13A.

FIG. 14 is a block diagram of a method for inhibiting the obstruction of the prostatic urethra after thermal ablation according to the present invention.

FIG. 15 is a block diagram of a method for detaching a conduit from a catheter or stent when the stent is positioned in a subject according to embodiments of the present invention.

FIG. 18 is a front view of yet another embodiment of a stent according to the present invention.

FIG. 18A is an enlarged view of a region of the stent shown in FIG. 18.

FIG. 19 is a front view of an additional embodiment of a stent according to the present invention.

FIG. 19A is an enlarged view of a region of the stent shown in FIG. 19.

DETAILED DESCRIPTION OF EMBODIMENTS OF THE INVENTION

The present invention now will be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the figures, certain elements or features may be exaggerated for clarity. Like numbers refer to like elements throughout.

Figure 1:
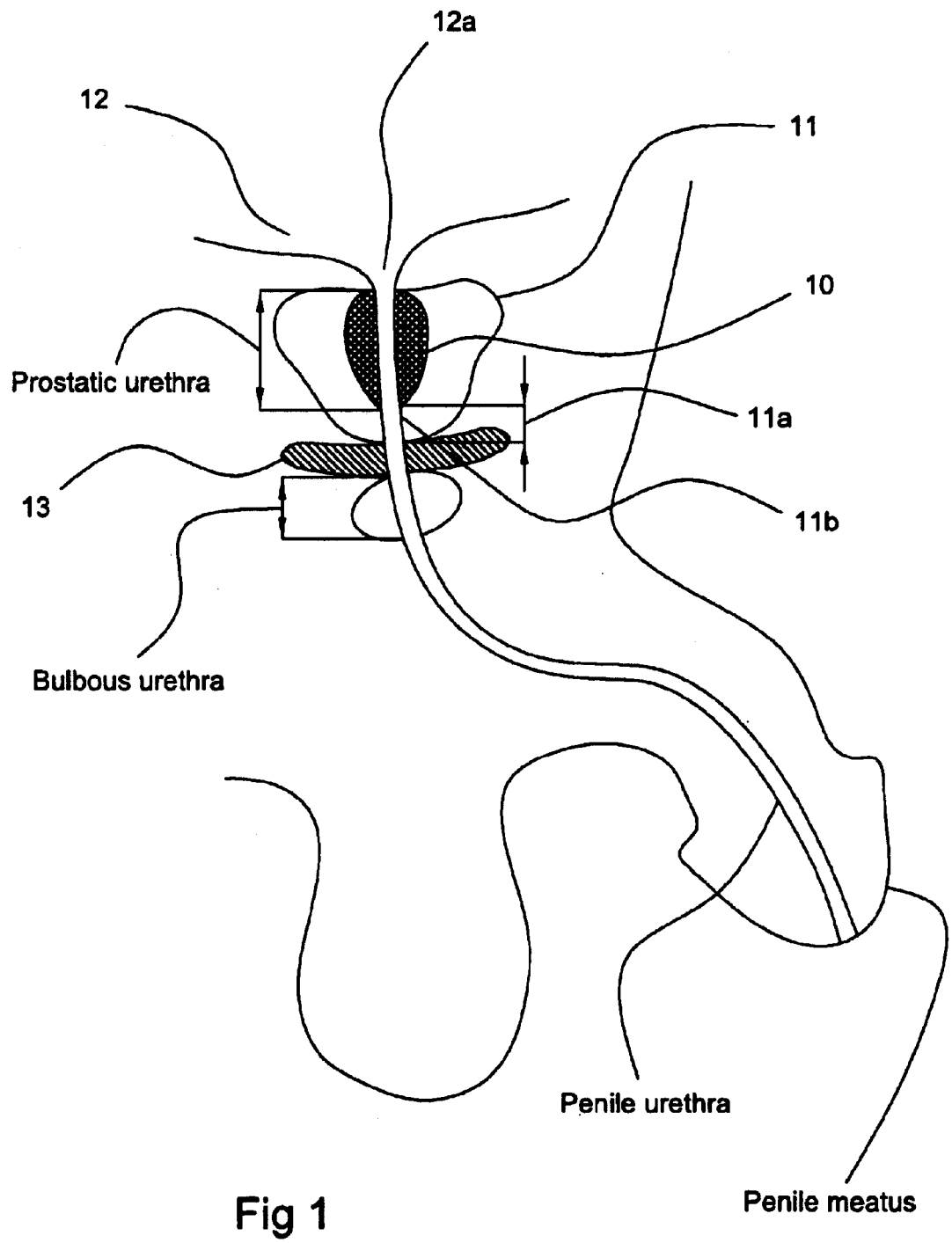
FIG. 1 is a schematic illustration of the anatomy of the male urethra showing a thermal ablation treatment region in the prostate.

Referring now to FIG. 1, the thermal ablation treatment region 10 is indicated by the lined region in the prostate 11. The term "thermal ablation" refers to exposing the targeted tissue to a temperature which is sufficient to kill the tissue. In certain embodiments, the thermal ablation is carried out by exposing the targeted tissue to thermocoagulation via a catheter inserted into the subject which is configured to direct circulating hot liquid heated external of the body of the subject to the targeted treatment region. Preferably, the tissue is exposed to an elevated temperature which is greater than or equal to about 45° C. for a predetermined period of time. In other embodiments, other treatment types can also be used such as surgical resection or other thermal therapies. The stents of the present invention may be appropriate for insertion in either treated or untreated natural lumens or body cavities such as blood vessels including arteries, the colon, the uterus, the cervix, the throat, the respiratory passages, the ear, the nose, and the like, to inhibit closure or restriction thereof.

In certain embodiments, the thermal ablation is directed to treating BPH. In so doing, the prostatic tissue can be exposed to a temperature which is at or above about 50° C.–62° C. for a treatment period which is about 20–60 minutes. In certain embodiments, the treatment temperature can be at about 60° C.–62° C. In other embodiments, temperatures of 45° C.–50° C. may be used. It is preferred that the BPH thermal ablation therapy be carried out in a localized treatment region within the prostatic urethra, the treatment region 10 being generally described as including the upper portion of the urethra in the prostatic urethra so as to extend generally below the bladder neck 12a and above the verumontanum 11b of the subject. Alternatively, the treatment region 10 may include the bladder neck 12a or a portion of the bladder neck itself. A suitable thermal treatment system and treatment catheter are available from ArgoMed, Inc. located in Cary, N.C. See also, U.S. Pat. Nos. 5,257,977 and 5,549,559 to Eshel, and co-assigned U.S. patent application Ser. No. 09/433,952 to Eshel et al, the contents of which are hereby incorporated by reference as if recited in full herein.

In certain embodiments, once the thermal ablation therapy has been delivered to the subject, the treatment catheter is left in position in the subject for an initial recovery period. This initial recovery period can be from about 12–72 hours, and preferably, about 24–48 hours. Leaving the treatment catheter in position for this initial period can reduce bleeding and subsequent blood clotting upon removal thereof.

In any event, as shown in FIGS. 2, 4, 5A and 5B, a post-treatment catheter or stent 20 is inserted into the penile urethra via the penile meatus and into a desired position in the prostatic urethra 11 (FIG. 1) relative to the treatment region 10. In untreated applications, the stent 20 can be used when desired and its use is not limited to post-therapeutic applications.

As shown, the stent 20 is a unitary body 20b which has a length such that it extends above the sphincter 13 when in position in the subject. The stent 20 also includes at least one fluid flow conduit or tube 25 having a length sufficient to extend from the stent body 20b to a position which is external of the subject when the stent 20 is in position in the prostatic cavity. The conduit 25 is configured with a shape and/or cross-sectional size, which is substantially smaller than the stent body cross-sectional size or width such that it is sufficiently small to allow normal function of the sphincter. The stent 20 also includes a localized tissue-anchoring balloon 22, which is in fluid communication with the conduit or tube 25 and a central lumen 23. As such, the stent 20 is sized and configured to reside in the subject above the sphincter 13. That is, unlike incontinence catheters or transurethral stent configurations, the unitary stent body 20b of the present invention is configured to reside entirely above the spinchter 13 so that only one or more substantially smaller diameter (or cross-section) tube(s) 25 extend below the subject's sphincter to exit the penile meatus. As only one or more tubes 25 extend through the sphincter 13, the stent 20 configuration allows natural operation of the sphincter 13 (i.e., the sphincter can close substantially normally with the stent 20 in position) thereby reducing the complexity and invasiveness of the device. Preferably, the width or outer diameter of the stent body 20b is about 6–9 mm and the conduit 25 is sized to be at least about 20–25 percent less than the cross-sectional width or outer diameter of the stent body, and more preferably the conduit has an outer cross-sectional width or diameter which is from about 0.5 mm–2.25 mm.

In order to anchor the stent 20 in a desired position or location within the prostate 11, (after the stent 20 is inserted into the prostate 11) the stent localized tissue anchoring balloon 22 or inflatable segment is inflated via a fluid introduced through the conduit 25 to an expanded configuration. When expanded, the anchoring balloon 22 is adapted to engage with prostatic tissue (when deflated, the stent body 20b preferably is configured as a smooth substantially constant profile body to allow for ease of insertion into the body). Preferably, the stent 20 is configured such that the tissue-anchoring balloon 22 engages with urethral tissue which is below the treatment region 10 but above the sphincter 13, and more preferably in the membranous urethra, and most preferably between the sphincter 13 and the verumontanum 11b.

As shown in FIGS. 2 and 5A, 5B, the tissue-anchoring balloon 22 is preferably configured to take on a shape which can be described as a pear shape, ramped or inclined shape, or frusto-conical shape, when expanded. This allows the profile of the tissue-anchoring balloon 22 to taper out from the top to the bottom, thereby inhibiting movement of the stent 20 toward the sphincter 13 when the sphincter 13 relaxes or opens. In addition, this shape may also inhibit upward movement of the stent body 20b toward the treatment region 10 or bladder 12, as the upper portion of the prostatic urethra, especially when the treated tissue is swollen, inflamed or suffering from edema, tends to close down or restrict the opening area in this region. Thus, the tapered anchoring balloon 22 which can be positioned in the in the membranous urethra will abut the restricted size of the urethral canal thereabove, in the treatment region, thereby inhibiting upward movement or migration of the stent 20. Of course, the present invention is not limited thereto and other localized balloon shapes may also be employed such as bulbous, elliptical, oval, cylindrical, accordion pleated, tapered fins (such as circumferentially disposed about the perimeter of the lower portion of the stent body), and the like.

As noted above, the tissue-anchoring balloon 22 is in fluid communication with the conduit 25 which is operatively associated with a valve 30 and a fluid inflation source (not shown). Valve 30 is well known to those of skill in the art and are available from medical suppliers, such as Alaris Medical Systems of Creedmoor, N.C. and San Diego, Calif. In operation, inflation media (liquid, gas, or a mixture of one or more of liquid, gas and/or a powder or solid (which may dissolve after exposure to the gas or liquid)) is directed into the conduit or tube 25 and up into the tissue anchoring balloon 22.

The stent body 20b can be configured with spaced apart tubular walls so that the gap between the walls form part of the inflation path (see e.g., FIG. 13A). As shown in FIGS. 4 and 5A, the conduit 25 is directly connected with an opening 26 in the tubular wall of the stent body 20b through which the inflation medium is directed. Suitable inflation media include gas, liquids, or solids/powders or mixtures thereof, including, but not limited to, air, noble gases such as nitrogen and helium, oxygen, water, and oils (such as cannola oil, olive oil, and the like). Preferably, the inflation medium is selected to be non-toxic and to reduce any noxious effect to the subject should the balloon integrity be compromised, accidentally rupture, leak, or otherwise become impaired during service. In certain embodiments, a liquid (or a substantially liquid media) be used to inflate at least the tissue anchoring balloon 22, to extend the time that the balloon 22 will remain substantially inflated during chronic or longer-term (during the post-treatment healing process) positioning in the body. Due to the thin wall of the inflatable balloon, air or gas may more easily migrate from the balloon allowing the balloon to deflate prematurely or to become more compressible (and potentially less effective to anchor in the desired location) as it loses inflation media.

FIG. 4 illustrates one embodiment of a stent 20 which includes externally visible indicia of the integrity of the inflated state of the lower inflatable portion 22 (inflation indicia can also be used to indicate the same about the bladder anchoring balloon 52, or two can be used, one for each as shown in FIG. 9A). As shown, this embodiment employs an external balloon, which is in fluid communication with the valve 30 and the lower inflatable portion 22 and positioned relative to the stent 20 such that it is located outside the body when the stent is in position in the subject. Preferably, as shown in FIG. 4, the external indicator balloon 75 is disposed proximate the valve 30 to provide a cushion between the valve and the penile meatus.

In operation, inflation media is directed into the conduit 25 through the valve 30 and an externally disposed balloon 75. The external balloon 75 inflates to a state which is representative of a fully inflatable state for the lower inflatable portion 22. The valve 30 is then closed and the external balloon 75 and the lower inflatable portion 22 are held in a desired inflated state. If the closed inflation system is compromised, the external balloon will deflate (reflecting the internal balloon has also been compromised and is deflating/deflated), and thus, provide a visually accessible means of identifying that the system is compromised. This can, in turn, allow a user or clinician to be alerted as to a potential malfunction, and can allow a user or clinician to re-inflate or inspect the position of the stent 20, preferably before the stent 20 shifts to an undesirable location within the subject. The means for externally visible indicia of the integrity of the inflated state can be used for one or all of the inflatable balloons on the stent (shown here to indicate the inflated state of the lower anchoring balloon 22). The means for the externally visible indicia of the integrity of the inflated state can be provided by other mechanisms, such as a "pop-up" indicator or sliding member operably associated with the valve 30 and the conduit 25 and/or a selected inflatable portion or balloon on the stent, the sliding member or indicator being configured to slide in a predetermined direction and present an externally visual indication when pressure in the closed inflation path (defined by the mechanism, the valve, the conduit, and the inflatable portion and/or balloon on the stent) drops below a threshold pressure level (not shown). Positive pressure valves are available from the Halkey-Roberts Co.

In certain embodiments, the stent body 20b is conformably configured such that it can follow the contours of the urethra while having sufficient rigidity to maintain a sufficiently sized opening in the central lumen 23 to allow urine drainage and or flushing or drug delivery during the healing period while in position. In certain embodiments, the stent body 20b is conformable but configured such that it is able to substantially maintain an opening in the central lumen when inserted and in position (and exposed to compressive swelling pressures in the localized treatment region) such that it maintains at least about 75% of the cross-sectional area, and preferably, at least about 90% or more of the cross-sectional area of central lumen 23 of the stent prior to insertion in the urethra. Of course, the cross-sectional shape of the lumen may alter from the non-inserted shape, depending on the pressure distribution of the tissue surrounding and contacting same. Stated differently, the unitary tubular stent body 20b is sufficiently conformable to yield to the contours of the subject's body as it is inserted therethrough into position in the prostate, yet sufficiently rigid to provide an open lumen when in position in the prostate and exposed to prostatic tissue which is exhibiting distress subsequent to undergoing thermal ablation therapy. Typically the stent body is able to maintain a sufficient opening when exposed to compressive pressures from the treated tissue on the order of about 7–21 psi.

In the embodiments shown in FIG. 2 and FIGS. 4–5A, 5B, the stent body 20b is configured with a substantially uniform static body shape (non-inflatable) apart from the lower inflatable anchoring balloon 22. Referring to FIG. 2, the upper end is open and preferably includes a series of offset openings 24 formed in the stent tubular body 20b and arranged around the perimeter thereof. This portion of the stent 20 enters the bladder and the additional openings 24 (apart from the central lumen 23) can facilitate urine entering into the central lumen 23 proximate the bladder 12 to travel through the stent body 20b.

Examples of suitable materials for the stent are thermoplastic elastomers, silicone, rubber, plasticized PVC, or other suitable biomedically acceptable elastomeric body. Typically, the stent unitary body 20b has a wall thickness of about 1.0 mm and a central lumen size of about 4.7–7.0 mm. As the prostate length can vary from subject to subject, the stent is preferably produced in a plurality of lengths in a range of from about 3–12 cm, and more preferably from about 4–10 cm.

As noted above, the stents 20 of the present invention are configured to reside above the spinchter 13. FIG. 2 also illustrates that the stent 20 may include external indicia of longitudinal movement which can alert the subject as to whether the stent 20 has migrated from its desired position. For example, a series of graduation marks 25g can be attached to or formed on the external conduit. Upon initial insertion, an appropriate indicia or marking 25a can be applied to a graduation mark residing at a predetermined number of graduation marks outside the penile meatus. If the stent 20 moves toward the bladder 12, the subject can look at the applied graduation mark on the conduit 25 and recognize that it is migrating closer to the lumen entry point of the penile meatus; on the other hand, if the stent body 20b moves toward the sphincter 13, an increased number of markings will be visible and the conduit 25 with the applied mark 25a will migrate away from the lumen entry point of the penile meatus.

The subject can be alerted that upon identification of a movement over a certain number of graduation marks i.e., 1–10 (which can correspond with predetermined distances such as mm or cm), depending on the spacing of the marks, to notify his physician so that appropriate action may be taken. The movement may indicate that healing is sufficient to allow removal altogether, or that undue physical activity may have exerted unusual forces onto the stent causing same to dislodge, such that removal and/or reinsertion may be required.

Alternatively, particularly for movement inward, the subject may be able to self-adjust the position of the stent body 20b by merely pulling on the conduit until the applied marking 25a once again resides at the appropriate number of marks away from the lumen entry.

In addition, a "stopper" can be applied to the conduit on a portion which is located external to the subject. The "stopper" can be configured and sized to resist entry into the opening in the penile meatus thereby inhibiting undue inward travel of the stent body 20b. The stopper can have any number of configurations and can be integral to or separate from the conduit itself. The stopper can be configured to be minimally invasive (non-irritating) to the user as it will be worn by same during use (not shown).

The stent 20 can also be configured with radiopaque markers to help identify its position for X-ray visualization. As such, X-rays can be taken at insertion/placement (initial positioning) and can also be taken periodically during the use of the stent or when there is a suspicion that the stent may have migrated from the desired location or merely to confirm proper positioning in the subject in situ. As shown in FIG. 5A, the radiopaque markers 77 can be circumferentially arranged on the stent either or both above 77u and below 77l the localized tissue anchoring balloon 22 so that the anchoring balloon 22 can be more readily accentuated and confirmed in the X-ray as located in the membranous urethra, above the sphincter. Alternatively, or in addition to, as shown in FIG. 4, one or more longitudinally extending radiopaque markers 77a can be arranged to extend substantially along the length of the stent at various radial positions (preferably at least 4 symmetrically separated and aligned about the cross-sectional width of the stent, typically at 90 degree radial separation to allow for X-ray identification irrespective of the image angle). The radiopaque markers are applied to block the transmission of X-ray for better contrast in images. The opacity, degree of contrast, and sharpness of the image may vary with material and type of process used to create the marker. The radiopaque marker(s) may be arranged on the stent by any suitable biocompatible marker technique such as non-toxic radiopaque coatings, inks, thin-films, paints, tapes, strips, shrink tubing, and the like. See e.g., Richard Sahagian, *Critical Insight: Marking Devices with Radiopaque Coatings*, Medical Device & Diagnostic Industry (May, 1999), also available at URL http://www.devicelink.com/mddi/archive/99/05/011.html. Other examples of radiopaque markers include polyolefin inks available as No-Tox® Medical Device Polyolefin Inks from Colorcon, and resin compounds with barium sulfate and/or bismuth such as is available from New England Urethane Inc. of North Haven, Conn. See also Danilychev et al., *Improving Adhesion Characteristics of Wire Insulation Surfaces*, Wire Technology International, March 1994 (discussing various treatments such as gas plasma treatment systems for medical products) which may be appropriate for use in the fabrication of the stent 20.

FIG. 5B illustrates that the stent 20 can include two conduits 25a, 25b, one in fluid communication with the lower inflatable anchoring balloon 22 and one in fluid communication with a medication delivery port 90. Medication, drugs, treatments, rinses, and the like can be introduced into the subject through an external medication port inlet 90i. The fluid (or mixture) is then directed to exit the delivery port 90 on the stent 20 after the fluid travels through the conduit 25b and released at the delivery port 90. In one embodiment, the medication port 90 is operably associated with a distribution channel 90c which extends circumferentially around the outer surface of the stent body 20b so as to allow the fluid to flow therein to facilitate a broader dispersion of the released fluid. The medication inlet port can be provided by any suitable valve/port device as is known to those of skill in the art. Suitable valve devices (for both the inflation system and the medication delivery system) are available from medical device manufacturers such as Alaris Medical Systems (SmartSite® system) and B. Braun. The medication can be used to reduce edema, inhibit bacterial infections, reduce the likelihood of UTI or treat the onset of UTI or otherwise promote healing and/or treatment.

FIG. 5B also shows the conduits 25a, 25b, relative to the sphincter illustrating (in dotted line) the inward movement of the conduits relative to the stent body 20b when in position, allowing the sphincter to function substantially normally when the stent 20 is proper position in situ.

FIG. 6A illustrates a stent 20 similar to that shown in FIGS. 4 and 5, but having an inflatable tissue-molding portion 42 above the tissue-anchoring portion 22. The inflatable tissue molding portion 42 is configured to extend proximate the treatment region 10 when the stent 20 is in position in the subject. The tissue-molding portion 42 can be substantially cylindrical when expanded to mold the opening in the treated region of the prostatic urethra to a width or outer diameter commensurate therewith as the ablated tissue heals to an increased opening size, prolonging the successful life of the treatment. In certain embodiments, the inflatable tissue-molding portion 42 is sized such that when inflated it presents an outer diameter or width of about 15–25 mm. The inflatable tissue molding portion 42 as well as the tissue-anchoring balloon 22 can be configured to be in fluid communication with the conduit or tube 25.

As shown in FIG. 6A, a fluid flow channel 44 can be formed in the walls of the stent body 20b intermediate the two inflatable portions 22, 42, in a manner similar to that discussed above, or a bridging conduit (not shown) can be used to bridge the two inflatable balloon segments 22, 42 and be in fluid communication with the tube 25. Alternatively, an additional tube can be added to inflate/deflate the inflatable tissue portion 42 such that the tissue-anchoring balloon 22 is in fluid isolation from the inflatable tissue portion 42 (such as shown in FIG. 9A for an alternative inflatable arrangement).

FIG. 6B illustrates that the open-ended stent 20 shown, for example, in FIG. 4, can alternatively (or in addition to) include an upper anchoring balloon 52 which is configured to reside against the bladder neck when in position and inflated. As shown this embodiment employs two separate conduits 25a, 25b, allowing the two balloons 22, 52 to be separately inflated and deflated.

FIGS. 7A and 7B illustrate an additional embodiment of a stent 20 according to the present invention. In this embodiment, the stent 20 includes a closed end portion 20e with at least one opening 27 formed spaced apart from the tip, the closed end portion 20e being adapted to be positioned in the bladder 12 to allow fluids to be flushed through the at least one opening (including drug delivery as needed) and/or to allow urine to drain therefrom. As before, the stent 20 includes a unitary body 20b which is configured to reside in the prostate such that the tissue anchoring balloon 22 is located below the treated region 10 and the non-inflatable shaft portion 20n of the stent body 20b extends along the treatment region 10. FIG. 8 illustrates that the stent 20 may also include an inflatable tissue portion 42 which is positioned intermediate the closed end 20e and the tissue-anchoring balloon 22 as discussed above.

FIGS. 3, 9A, and 9B illustrate yet another embodiment of the present invention. In this embodiment, the stent 20 includes an upper bladder-anchoring balloon 52 as well as the (lower) tissue-anchoring balloon 22. As shown in FIG. 3, the bladder-anchoring balloon 52 resides against the bladder neck of the subject, thereby securely positioning the stent 20 in the prostate relative to the bladder 12. As the inflated or expanded balloon 52 resides against the bladder neck, movement toward the sphincter 13 is inhibited. Similarly, the tissue-anchoring balloon 22 located on the other opposing end portion of the stent inhibits movement toward the bladder (thus providing bilateral anchoring in the prostate). As shown, the intermediately located non-inflatable portion 20n of the stent shaft or body 20b is located adjacent the treatment region 10. In this embodiment, the stent body 20b may have a length which is greater than the open-end length as it is configured to enter the bladder. As such, the length of the stent body 20b below the upper balloon 52 may be provided in several sizes from about 3–12 cm, and preferably from about 4–10 cm. The same reasoning can be applied to the closed end embodiments shown for example in FIGS. 7A, 7B, and 8 (that is, the length of the stent 20 below the closed end portion and drainage eye(s) 27 may be on the same order as that described above).

In certain embodiments, the upper anchoring balloon 52 is separately inflatable to allow this balloon 52 to be inflated before the lower balloon 22. This can reduce the likelihood that the upper balloon 52 will be inflated below the desired location (potentially introducing damage to the bladder neck or the upper portion of the prostatic urethra) and facilitate proper positioning of the stent 20 in the prostate relative to the bladder and above the sphincter 13.

As shown in FIG. 3 and FIG. 9A, two conduits 25a, 25b extend from the stent body 20b, each in fluid communication with a corresponding upper or lower balloon 52, 22, respectively. FIG. 9B illustrates the stent 20 with both the upper and lower anchoring balloons 52, 22 in a deflated state. In this embodiment, a single tube 25 is used to inflate both the upper and lower balloons 52, 22 through a fluid opening positioned relative to each one 26.

FIG. 9A also illustrates another embodiment of the present invention. In this embodiment, a conduit 225 is releasably attached to the stent body 20b and is in fluid communication with the upper anchoring balloon 52. In operation, the stent 20 is inserted into position as described above, and the upper anchoring balloon 52 is inflated through conduit 225 to position the stent in a desired location relative to the bladder neck landmark. The lower balloon 22 is then inflated to hold the stent 20 in position above the sphincter 13. A tensile force shown by the arrow labeled "$F_{pull}$" is applied to remove the conduit 225 and deflate the anchoring balloon 52. This can reduce the number of conduits (and the invasiveness of the design) extending out of the subject during the healing period. Preferably, the conduit 225 and/or valve 30 operably associated therewith which is configured to releasably detach from the stent 20 is conspicuously identified by an identifier 225i so that an operator may easily identify the proper conduit to which to apply the release force to. For example, the releasable conduit 225 and/or its associated valve member 30 can be striped, labeled, painted, colored, or otherwise configured with visually apparent indicia.

Any suitable attachment means can be used to releasably secure the conduit 225 to the stent body 20b, such as mechanical or chemical means including, but not limited to, adhesives, heat bonding, chemical, or UV cured bonding of the conduit 225 to the stent body 20b so as to releasably attach to the stent body 20b. The attachment can be located at any suitable location along the stent body 20b or at the fluid entry 26 to the upper balloon 52, but is preferably arranged such that it is along the inner wall of the stent body to provide for easier insertion and protect it from handling degradation and/or stress or punctures. Preferably, the releasable attachment is configured so as to remain attached when exposed to small tensile or torsional forces typical of handling and at insertion, but yields at tensional forces above about 2–10N. Examples of attachment systems include PlasticWeld Systems Catheter Manufacturing Equipment from Plastic Weld Systems located in Nefane, N.Y.; the Novacure™ (referencing U.S. Pat. No. 5,521,392, the contents of which are hereby incorporated by reference as if recited in full herein), the UV 75, and the Ultracure 100SS Plus all from EFOS Inc, of Mississauga, Canada; the Green Spot UV Cure System from UV Source Inc, of Torrance, Calif.; the Medi-Cure™ MC Curing Spot and Flood Lamps (and other products) from DYMAX Corporation located in Torrington, Conn. Suitable UV adhesives are well known in the art. Examples include CTH adhesives known as model numbers 201 through 204 CTH, available from DYMAX Corporation of Torrington, Conn., and Permabond Adhesives for the medical device industry from Permabond Engineering Adhesives located in Englewood, N.J.

FIG. 10 illustrates the embodiments of FIGS. 3, 9A or 9B with a third inflatable portion, an intermediate inflatable tissue molding segment 42 as discussed for other embodiments above. As before, this embodiment may include one, two, or three or more conduits 25. Preferably, this stent 20 includes two conduits 25a, 25b configured such that the upper balloon 52 is in fluid isolation from the remaining intermediate and lower balloons 42, 22. As before, the conduit 25b shown for the upper balloon 52 may be configured to be releasably detachable from the stent body 20b once the stent 20 is in the desired location in the prostate. As shown and discussed above, the conduit 25 is substantially smaller in cross-sectional width than relative to the cross-sectional width of the stent body 20b.

Figure 17:
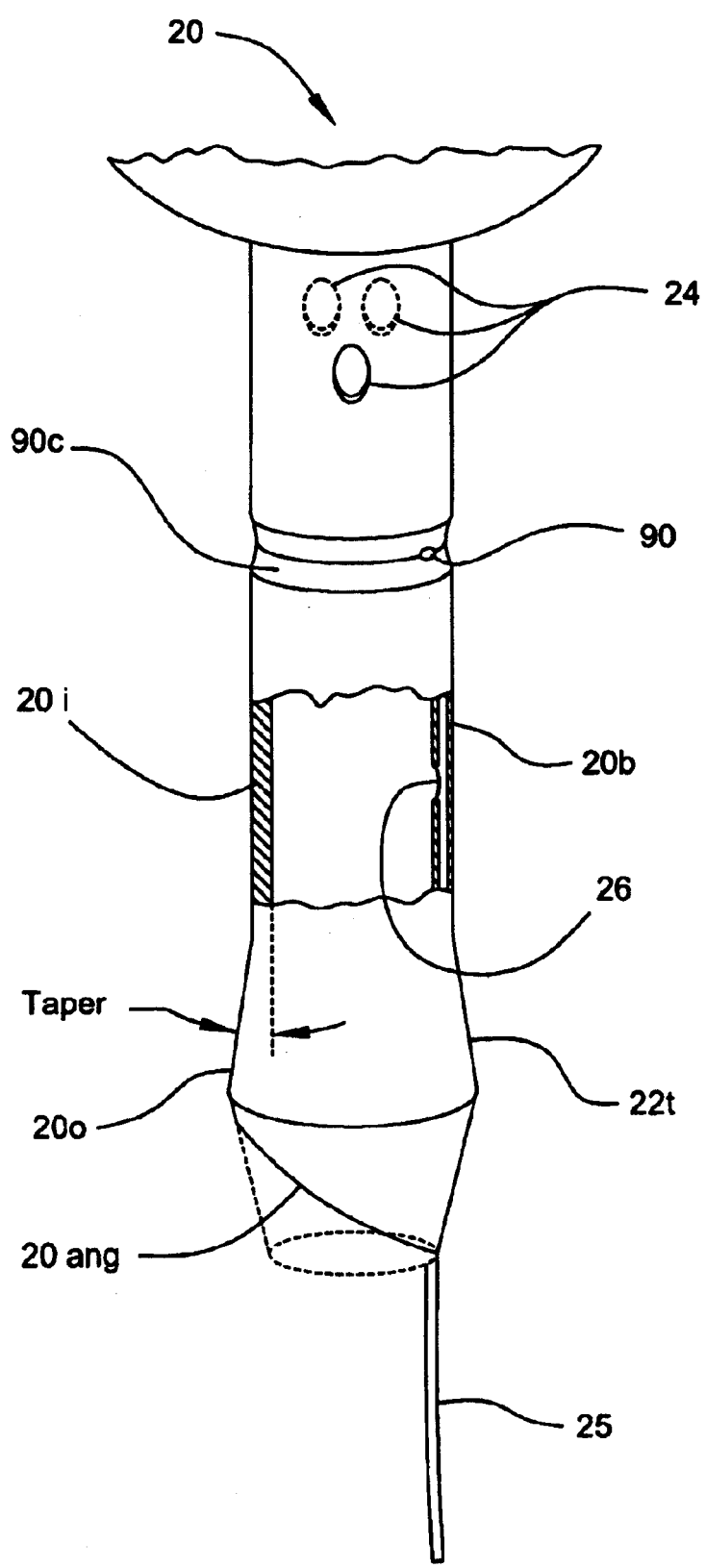
FIG. 17 is a front view of an alternate embodiment of a stent according to the present invention.

As shown in FIG. 17, the stent body 20b may be configured with alternate tissue-anchoring means. As shown, the lower portion of the stent body 20b tapers 22t laterally outwardly a distance relative to the upper portion. In certain embodiments, this taper can be configured such that the outer wall 20o increases no more than about 7 degrees radially outward along the taper profile line (shown by the arrows drawn from the outer surface to the inner wall 20i). This embodiment also illustrates that the bottom of the stent body 20b can have a diagonal shape, i.e., is angled 20ang across the width of the stent body 20b. As is also shown, the stent body 20b can include a drug delivery port 90 thereon.

In certain embodiments, the port 90 is in fluid communication with at least one fluid conduit 25 which can direct a rinse, medicament, or other fluid thereto. In some embodiments, the stent body 20b can have at least one liquid channel 90c formed circumferentially therearound. The liquid channel 90c is preferably in fluid communication with the drug delivery port 90. In operation, a saline or other biocompatible non-toxic rinse, or drug, treatment substance, or medicament, can be directed into the conduit and out of the port 90 and into the channel 90c. The channel 90c can thus distribute the liquid around the treatment region, which if merely ejected from the port may be localized to the region facing the port. The liquid channel 90c can be notched into the stent body or a region on the stent body 20b, which has a reduced wall thickness relative to one or more of the adjacent upper and lower portions of the stent body. The delivery port 90 may be also a plurality of ports circumferentially and/or axially spaced apart about the perimeter of the stent body 20b (not shown).

FIG. 18 illustrates another tissue anchoring means, a plurality of inflatable portions 322. The plurality of inflatable portions 322 present a ribbed or ridged profile which engages with the urethra and inhibits movement upward when in position. It is noted that, although shown as a series of aligned and serially connected frusto-conical inflatable portions 322, other shapes and configurations can also be employed to present a ribbed or ridged profile. As shown, the bladder-anchoring balloon 52 inhibits movement, and more particularly, is shaped and oriented in this embodiment to inhibit downward movement. Although shown as extending along the length of the stent body 20b, the inflatable portions 322 can be configured on the stent body 20b such that they extend only about a portion of the length of the stent body 20b. For example, so that a plurality of inflatable portions 322 are located only about the bottom portion of the stent body (not shown).

FIG. 19 illustrates yet another embodiment of a stent 20 according to the present invention. As shown, this embodiment includes an increased elastic portion 190 disposed about the stent body 20b such that it is above the lower anchoring balloon 22 (or lower anchoring means). The increased elastic portion 190 can be formed in a number of ways so as to allow tensional stretch (or collapse) in the stent body 20b to help locate and/or position the stent 20 in the desired location. For example, this region can be configured from a different material relative to the adjacent upper and lower regions of the stent body 191u, 191l, a notched region, a reduced wall thickness region, or by introducing symmetrically spaced windows about the circumference of the stent body 20b. In operation, upon inflation of the bladder-anchoring balloon 52 and positioning of the lower tissue-anchoring balloon 22 in the membranous urethra, upon inflation the stent body 20b may be pulled upward while the tissue-anchoring balloon is pulled downward. Therefore, introducing an elastic portion 190 between the two balloons, 52, 22, respectively, can allow the stent body to stay positioned in its desired location with enough stretch as to inhibit the introduction of undue tensile forces onto the stent body between the two balloons 52, 22 which can be caused by the configuration of the anatomy of the subject. The elastic portion 190 may also inhibit the introduction of unnecessary opposing locational forces of the respective balloons 52, 22 onto the surrounding tissue (i.e., a downward force onto the bladder neck and an upward force at the membranous urethra proximate or the prostatic urethra). The elastic portion 190 can also be configured to act as the medication/rinse channel 90c as discussed above.

As, in certain embodiments, the stent can resides in the body for between 2–14 days (and potentially even longer), surface or other treatments may also be applied to, or integrated into, the stent 20 to achieve one or more of increased lubricity, low coefficient of friction (each for easier insertion) as well as increased tissue biocompatibility such as resistance to microbial growth and/or configured to reduce the incidence of UTI. In one embodiment, the stent body 20b comprises a material, at least on its exposed surfaces, which can inhibit the growth of undesirable microbial organisms while the stent 20 is held in the body during the healing period as noted herein. Preferably, the stent is coated with a biocompatible antimicrobial solution or coating which can inhibit the growth of bacteria, yeast, mold, and fungus. One suitable material may be the antimicrobial silver zeolite based product available from HealthShield Technologies LLC of Wakefield, Mass. Another alternative is a Photolink® Infection Resistance antimicrobial coating or a hemocompatible coating from SurModics, Inc. of Eden Prairie, Minn. The coating may also include other bioactive ingredients (with or without the antimicrobial coating), such as antibiotics, and the like. One product is identified as LubriLAST™ lubricious coatings from AST of Billerica, Mass.

In addition to, or alternatively, the stent can be configured with a biocompatible lubricant or low-friction material to help reduce any discomfort associated with the insertion of the device into the body. Coatings which may be appropriate include coatings which promote lubricity, and wettability. For example, a hydrophilic coating which is applied as a thin (on the order of about 0.5–50 microns thick) layer which is chemically bonded with UV light over the external surface of the stent 20. One such product is a hydrophilic polymer identified as Hydrolene® available from SurModics, Inc., of Eden Prairie, Minn. Other similar products are also available from the same source. Still further, the stent 20 can be configured not only to provide the lubricious coating but to also include bioactive ingredients configured to provide sustained release of antibiotics, antimicrobial, and anti-restenosis agents, identified as LubrilLast™ from AST as noted above.

FIGS. 11A–11F illustrate a sequential series of operative deployment of the stent 20 into the body of the subject. FIG. 11A illustrates the stent 20. FIG. 11B illustrates one embodiment of a pusher or insertion guide 120 configured to extend through the central lumen 23 of the stent and used to insert the stent 20 into position in the subject. The insertion guide or pusher 120 includes at least one outwardly expandable fixation balloon(s) 136 and an anchoring or positioning balloon 152 positioned on a distal end portion thereof. The fixation balloon may be single balloon which is elongated and extend along the length of the stent body 20b or, as shown, may be a single localized fixation balloon located to engage with a distal or upper portion of the stent body 20b. A plurality of fixation balloons may also be used (not shown). As shown, the guide 120 also includes an elongated body, which is substantially longer than the stent body 20b.

FIG. 11C illustrates the insertion guide 120 inserted into the stent 20 such that the upper or distal end portion of the guide 120 extends through the open distal end of the stent 20. The fixation balloon 136 is then inflated to snugly hold the stent 20 affixed to the insertion guide 120. The elongated insertion guide 120 has a length which extends a distance out of the bottom or proximal end of the stent. The conduit 25 can reside along the outer perimeter of the insertion guide or can reside in a groove configured to hold same therein during insertion into the body.

As shown in FIG. 11D, the guide 120 inflatable (bladder) anchoring balloon 152 is expanded after the guide 120 and stent 20 are in position in the subject (such as in the prostate). As shown in FIG. 11E, the local tissue-anchoring balloon on the stent 22 is then inflated. Next, as shown in FIG. 11F, the guide upper anchoring balloon 152 and fixation balloon 136 are deflated so that the guide 120 can be slidably removed from the stent 20 leaving the stent in position (in the prostate). Other suitable guides and or pushers are well known to those of skill in the art. For additional description of guides with inflatable attachment or fixation means (which laterally expand) to hold the guide to inner wall of the stent 20 until the stent is in the desired location, see U.S. Pat. No. 5,916,195 and co-pending and co-assigned U.S. patent application Ser. No. 09/239,312, the contents of which are hereby incorporated by reference as if recited in full herein. After the healing period, the stent 20 can be removed by deflating the lower balloon 22 and pulling on the conduit 25.

Referring now to FIG. 12, one embodiment of a unitary body stent 20 and insertion guide 120 similar to that shown in FIGS. 11A–F is shown. In this embodiment, the stent includes spaced apart walls 20w1, 20w2 which may help retain the desired conformable stent configuration in operative use. That is, the stent 20 is configured to be conformable to the contours of the urethra upon insertion but is also sufficiently rigid to hold the central lumen size to a size which is substantially the same in the prostate as when the stent is external of the subject (i.e., it does not collapse to close off the passage or central lumen in response to the pressure of the ablated tissue in the prostate). The two spaced apart walls 20w1, 20w2 may also be connected with interconnecting structural baffle or support means, particularly in the portion which is configured for placement in the treatment region (not shown). See e.g., co-pending and co-assigned U.S. Provisional Patent App. Ser. No. 60/248, 109, the contents of which are hereby incorporated by reference as if recited in full herein. The conduit 25 can be attached to the stent body 20b to direct inflation medium or fluid into the gap between the walls, or the conduit 25 can be attached to enter the external wall 20w1 to inflate the lower balloon 22.

The guide 120 is configured with two separately inflatable portions: the elongated portion 136, which expands to affix to the inner surface of the inner wall 20w2; and the upper anchoring balloon 152. As shown, the guide 120 is also configured with a closed end but includes drainage and or flushing orifices 127 above the anchoring balloon 152. In operation, the guide 120 delivers the inflation medium into an inlet/outlet or port 136i in fluid communication with the fixation balloon portion through a valve 230 and associated inflation source 236. Similarly, to anchor the stent and guide in the prostate at the bladder neck, the upper anchoring balloon 152 on the guide is expanded via fluid entering the port 126 (and subsequently leaving upon deflation). Fluid is directed from an inflation medium through a valve 230' and an associated inflation source 252. As shown, the guide 120 includes a central drainage lumen 123 which is in fluid communication with the bladder of the subject (when in operative position) and is configured to drain and/or flush fluids therebetween.

Figure 13B:
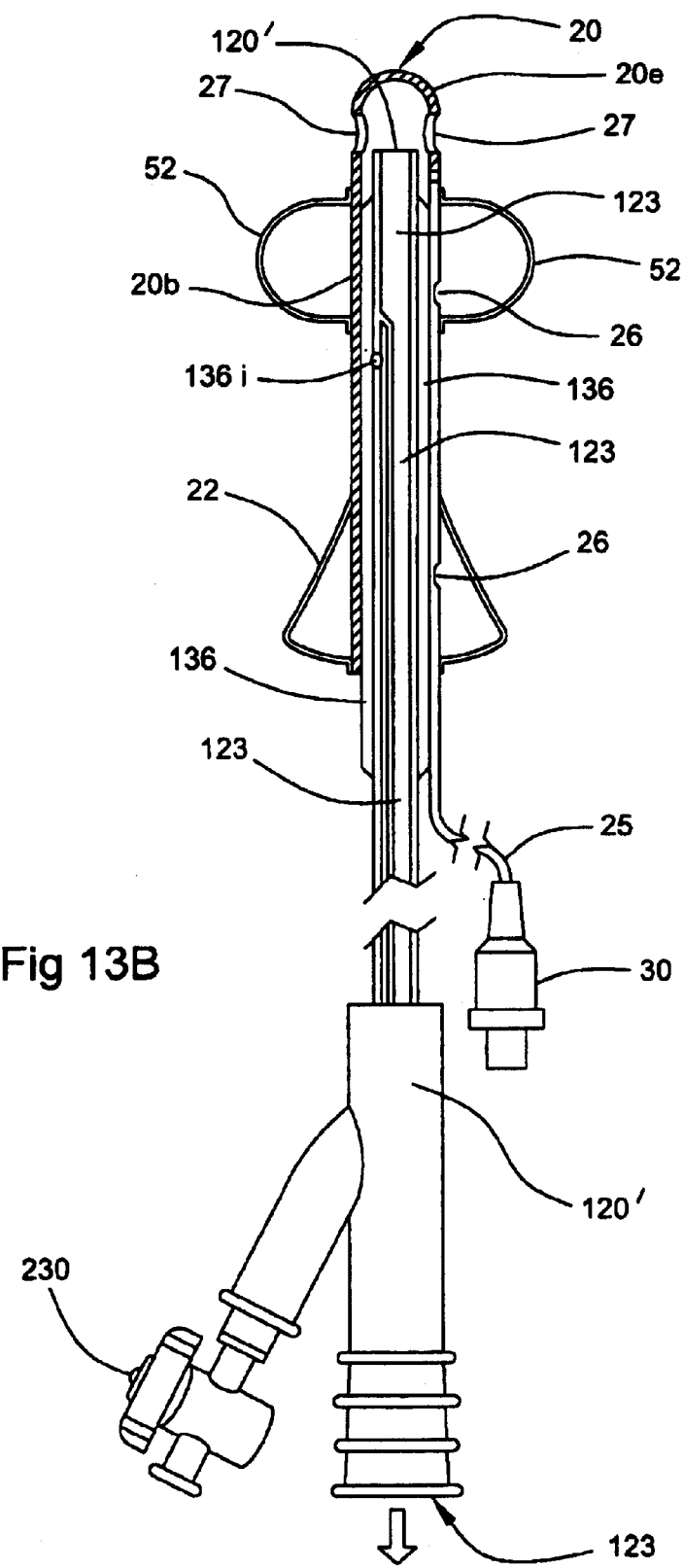
FIG. 13B is an enlarged side section view of the stent shown in FIG. 13A with an alternate embodiment of a pusher/insertion guide positioned therein.

FIG. 13A illustrates an embodiment similar to that shown in FIGS. 9A and 9B. As shown, the stent 20 is configured with the upper anchoring balloon 52, so the inflatable guide 120' (FIG. 13B) includes an open end with a drainage lumen 123 therethrough. The inflatable guide 120' (FIG. 13B) includes an fixation segment or balloon 136 as discussed under the embodiment shown in FIG. 12, but only one valve 230 and associated guide inflation source is needed. In operation, once the stent upper anchoring balloon 52 is in position and inflated to secure the stent 20 in position, the guide fixation balloon portion 136 can be deflated and the guide 120' easily slidably removed from the stent 20, leaving the stent 20 in its desired position in the body fixed relative to the bladder and residing above the sphincter, as discussed above.

It will be appreciated by those of skill in the art that other guides or pushers can also be used to insert and position the stent in the prostate. For example, guide wire or stylet placement systems are well known. Guide wires are typically used with a stent having an open end such as shown in FIG. 2, while stylets are used with closed end or tips (such as shown in FIG. 3) to inhibit the stylet from contacting the urethra and potentially causing injury thereto.

In addition, although the closed end configurations of the stent 20 shown herein have been illustrated as substantially upright, they can also be curved into other configurations such as Coude or Tiemen.

Turning now to FIG. 14, a method for inhibiting the obstruction of the prostatic urethra after thermal ablation (or resection or other procedure) according to the present invention, is shown. First, a prostatic tissue is treated such as thermally ablated (Block 400). Subsequent to treatment, a stent having a unitary body with a first cross-sectional area, and a conduit attached thereto, the conduit having a second cross-sectional area, the second cross-sectional area being substantially less than the first, is inserted into the penile meatus and up along the penile urethra until the body of the stent is positioned in a desired location such that it resides in the prostate above the sphincter (Block 410). A (lower) tissue-anchoring balloon is inflated to secure the stent in the desired location (Block 420). After a period of about 2–14 days, the stent lower anchoring balloon is deflated and the stent is removed by pulling on an externally exposed end of the conduit (Block 430).

FIG. 15 is a block diagram of a method for detaching a conduit from a catheter or stent when the stent is positioned in a subject. First, a stent with a releasably attached or detachable conduit is inserted into the natural lumen of the body such that a portion of the conduit remains external of the subject (Block 500). Next, a tensile force is exerted onto the detachable conduit (by pulling the exposed portion of the conduit), forcing the conduit to detach from the catheter or stent while leaving the stent in position in the body (Block 510).

In certain embodiments, the detachable conduit is in fluid communication with a bladder-anchoring balloon and the bladder-anchoring balloon deflates responsive to the detachment of the first conduit. The stent can include a second conduit separate from the first which is configured to direct an inflation media (preferably comprising a liquid) into a lower inflatable segment on the stent when the first conduit is detached. In operation, the bladder neck-anchoring balloon is inflated after insertion for positioning the stent in the subject relative to the bladder neck (where the bladder anchoring balloon resides).

In certain embodiments, the positioning step will be carried out such that the stent body is positioned above the sphincter and the lower anchoring means (such as the lower balloon) is located between the verumontanum and the sphincter (in the membranous urethra). To anchor the sent after the bladder anchoring balloon is in position and inflated (via a second conduit), the lower inflatable member is inflated. It is subsequent to this second inflation that the detachable conduit is removed.

Figure 16:
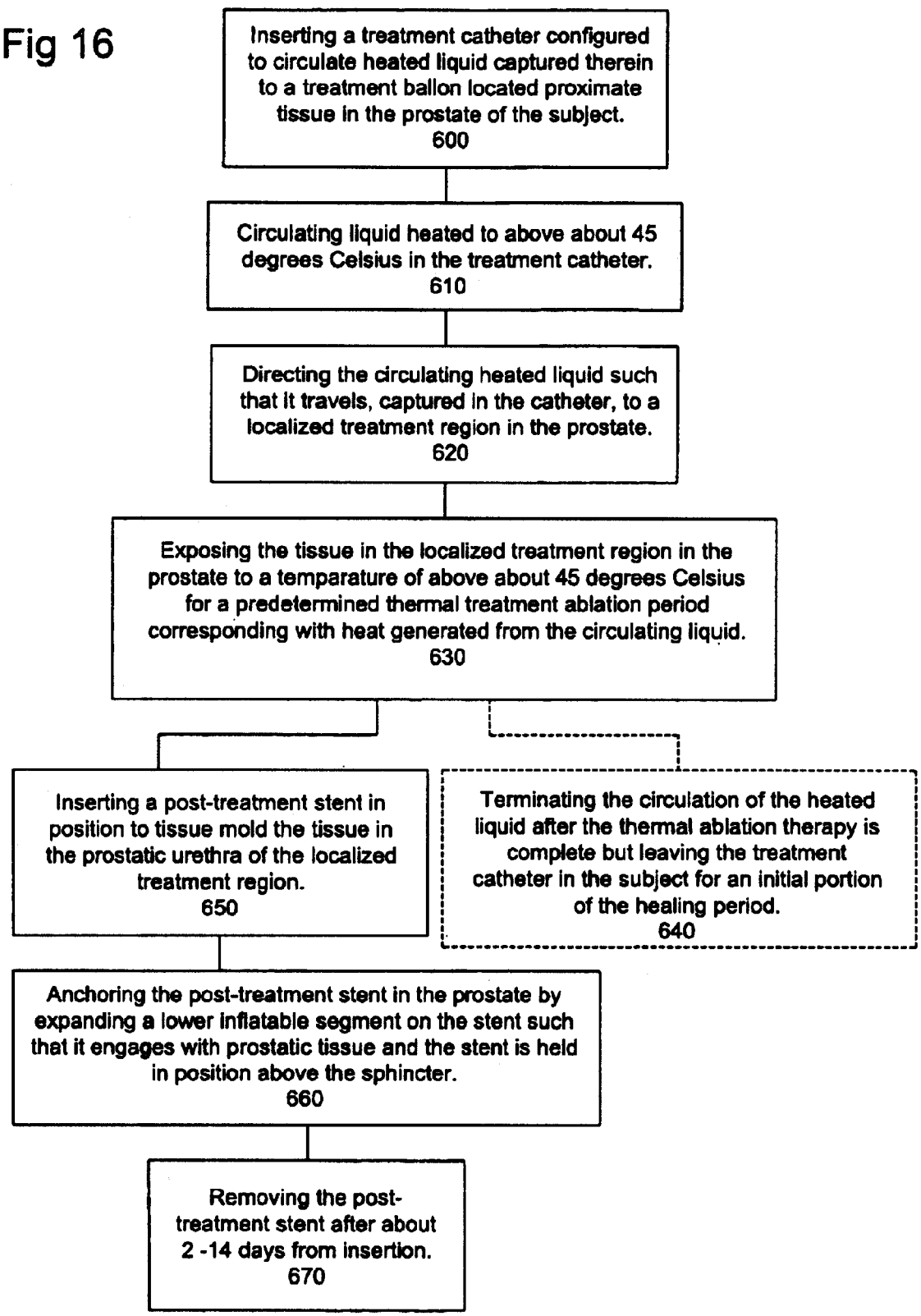
FIG. 16 is a block diagram of a method for treating BPH according to embodiments of the present invention.

FIG. 16 is a block diagram of a method for treating BPH according to embodiments of the present invention. The method includes inserting a treatment catheter configured to circulate heated liquid into the prostate of the subject (Block 600) and then circulating liquid heated to above 45° C. (Block 610). The circulating heated liquid is directed through the catheter to a treatment balloon such that it travels, captured in the catheter, through the penile meatus, along the penile urethra the bulbous urethra, and the membranous urethra to a localized treatment region in the prostate (Block 620). The tissue in the localized treatment region in the prostate is exposed to a temperature above about 45° C. for a predetermined thermal ablation treatment period by exposure to the heated circulating liquid (typically at about 50–62° C. for more than about 30 minutes) (Block 630). As noted above, the localized treatment region can be an upper portion of the prostatic urethra, leaving the urethra below the prostatic urethra about the membranous urethra, non-ablated. This is accomplished, in circulating systems, which heat remotely, by insulating the shaft of the treatment catheter up to the treatment balloon to inhibit the exposure of non-targeted tissue to ablation temperatures.

In other embodiments, the circulating fluid can be heated to lower treatment temperatures, such as less than 45° C. (such as 35° C.–44° C.) or may be cooled to provide cooling at the localized tissue region.

In any event, after the thermal therapy is completed, the circulating heated water is partially (and preferably, totally) removed from the treatment catheter. In certain embodiments, the treatment catheter may be left in position in the subject for an initial portion of the healing process (the initial portion including about the first 12–72 hours, and more preferably about 24–48 hours) (shown by broken line to indicate that this is optional) (Block 640). This delay in removal of the treatment catheter can reduce the likelihood or amount of bleeding and subsequent blood clotting caused by premature removal of the treatment catheter.

A tissue-molding stent is inserted into the prostate immediately after the thermal treatment or after a delay (Block 650). The stent can be anchored in position in the prostate by inflating a localized balloon portion thereon such that it engages with the tissue of the subject and allows normal operation of the sphincter (Block 660). The post-treatment stent is removed from the subject, after the tissue anchoring balloon (and as applicable, the bladder anchoring balloon) is deflated, typically after about 2–14 days from insertion (Block 670).

It will be understood that one or more blocks of the block diagrams and combinations of blocks in block diagram figures can be implemented or directed to be carried out by computer program instructions. These computer program instructions may be loaded onto a computer or other programmable data processing apparatus to produce a machine, such that the instructions which execute on the computer or other programmable data processing apparatus create means for implementing the functions specified in the flowchart block or blocks. These computer program instructions may also be stored in a computer-readable memory that can direct a computer or other programmable data processing apparatus or associated hardware equipment to function in a particular manner diagrams.

Although described herein as suitable for a prostatic stent, it will be appreciated by those of skill in the art that the releasable or detachable attachment configurations as well as the elastic region and other features of the stents of the instant invention may be applied to other catheter or stent configurations, as well as to guides or pushers for placing and locating catheters and/or stents. In addition, the detachable conduits can be tubular, as shown, or can be alternatively configured, such as a line, string, linkage, or other small cross-sectional member which has a length which makes it externally accessible when the stent or guide is in the body. Using two or more lines while positioning transurethral stents in the desired internal body lumen position may reduce angular disorientation between the two members, while also reducing the number of lines (or size of sleeves) extending from the subject during use. In addition, the detachable or releasable line or conduit may also be used for other applications such as for catheters, guides, or stents and the like configured for insertion in natural lumens or body cavities such as blood vessels (including, but not limited to, arteries), the rectum, the colon, the cervix and/or uterus, the bladder, the throat, the ear, the nose, passages of the heart and/or associated valves, the respiratory system, the esophagus, and the like.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A prostatic stent configured for insertion into the urethra of a male subject, the urethra generally including, in serial order from the externalmost portion to the internal portion, the penile meatus, the penile urethra, the bulbous urethra, the sphincter, the membranous urethra, the prostatic urethra, the bladder neck and the bladder, said prostatic stent comprising:
   a unitary tubular body having a central lumen extending therethrough and a first cross-sectional width thereacross;
   a tissue-engaging inflatable balloon positioned on a lower perimeter portion of said unitary body; and
   at least one conduit having opposing upper and lower end portions with a fluid lumen formed therein, a portion of said upper end attached to said unitary tubular body such that it is in fluid communication with said inflatable balloon, said conduit having a second cross-sectional width, the second cross-sectional width being less than said first cross-sectional width;
   wherein, in position in the subject, said stent is configured such that said unitary body resides above the sphincter and said conduit extends through the sphincter and out of the penile meatus of the subject, and wherein said conduit is sized and constructed such that it allows substantially natural closing of the sphincter when in position in the subject.

2. A prostatic stent according to claim 1, wherein said unitary tubular body is configured such that a contiguous major portion of the length of said body is non-inflatable, and wherein said contiguous major portion is located above said inflatable tissue engaging anchoring balloon.

3. A prostatic stent according to claim 1, further comprising an upper anchoring balloon disposed about an upper portion of said unitary tubular body.

4. A prostatic stent according to claim 1, wherein a selected one of said at least one conduits is releasably attached to said unitary tubular body such that it can detached in situ from the stent by pulling on an end portion of said conduit without dislodging the unitary body from a desired location in the subject, and wherein said selected releasably attached conduit is configured to be readily visually identified externally when said stent is in position in the subject.

5. A prostatic stent according to claim 1, further comprising an intermediately positioned tissue-molding balloon disposed about said unitary tubular body.

6. A prostatic stent according to claim 1, wherein said unitary tubular body is sufficiently conformable to yield to the contours of the subject's body as it is inserted therein, yet sufficiently rigid to provide an open lumen when in position in the prostate and exposed to prostatic tissue which is exhibiting distress subsequent to undergoing thermal ablation therapy.

7. A prostatic stent according to claim 1, wherein at least one of said at least one conduits is configured with externally visible indicia of movement.

8. A prostatic stent according to claim 1, wherein said unitary body has a length which is about 4–10 cm.

9. A prostatic stent according to claim 1, wherein said unitary tubular body includes a pair of spaced apart walls which are configured to define at least one fluid flow channel therebetween.

10. A prostatic stent according to claim 1, wherein said unitary body has opposing upper and lower ends, wherein said upper end is configured to enter a distance into the bladder, and wherein said upper end is open.

11. A prostatic stent according to claim 2, Wherein a series of spatially separate apertures are formed in said unitary tubular body and arranged about the perimeter of a portion of said upper end, and wherein said apertures are in fluid communication with said central lumen.

12. A prostatic stent according to claim 3, wherein said unitary tubular body has opposing upper and lower ends, wherein said upper end is configured to enter a distance into the bladder, and wherein said upper end is closed, and wherein said stent body further comprises a urinary drainage port in fluid communication with said central lumen and disposed longitudinally spaced apart from said closed end in a direction which is toward said lower end of said unitary body, and wherein said conduit comprises a region with increased elasticity intermediate said tissue engaging balloon and said upper anchoring balloon.

13. A prostatic stent according to claim 1, wherein said at least one conduit includes two conduits.

14. A prostatic stent according to claim 13, wherein said two conduits are in fluid communication.

15. A prostatic stent according to claim 13, wherein said two conduits are in fluid isolation.

16. A prostatic stent according to claim 1, wherein said tissue engaging inflatable balloon is configured when expanded such that it has a profile which tapers to increase in width from top to bottom.

17. A prostatic stent according to claim 1, further comprising an externally visible indicia of the inflation status of said tissue-engaging inflatable balloon.

18. A prostatic stent according to claim 1, wherein said stent tubular body is configured with a hydrophilic lubricant.

19. A prostatic stent according to claim 1, wherein said stent tubular body is configured with an antimicrobial agent.

20. A set of prostatic stents each configured for insertion into the urethra of a male subject, the urethra generally including, in serial order front the external most portion to the internal portion, the penile meatus, the penile urethra, the bulbous urethra, the sphincter, the membranous urethra, the prostatic urethra, the bladder neck and the bladder, said set of prostatic stents-comprising:
  (a) a first prostatic stent comprising:
    a unitary tubular body having a central lumen extending therethrough, a first length, and an associated cross-sectional width thereacross;
    a tissue engaging inflatable balloon positioned on a lower perimeter portion of said unitary body; and
    at least one conduit having opposing upper and lower end portions with a fluid lumen formed a portion of said upper end attached to said unitary tubular body such that it is in fluid communication with said inflatable balloon, said conduit having a second cross-sectional width, the second cross-sectional width being substantially less than said first cross-sectional width;
  (b) a second prostatic stent comprising:
    a unitary tubular body having a central lumen extending therethrough, a second length and an associated cross-sectional width thereacross;
    a tissue engaging inflatable balloon positioned on a lower perimeter portion of said unitary body; and
    at least one conduit having opposing upper end lower end portions with a fluid lumen formed therein, a portion of said upper end attached to said unitary tubular body such that it is in fluid communication with said inflatable balloon, said conduit having a second cross-sectional width, the second cross-sectional width being substantially less than said first cross-sectional width,
    wherein, in position in the subject, each of said stents is configured that said unitary body resides above the sphincter and said conduit extends through the sphincter and out of the penile meatus of the subjection, and wherein said conduit is configured such that it allows substantially,natural closing of the sphincter when in position in the subject, and further wherein said first stent unitary body has a different length than said second stent unitary body.

21. A set of prostatic stents according to claim 20, wherein said conduits of said first and second stents comprise a series of externally visible graduation marks thereon.

22. A prostatic stent configured for insertion into the urethra of a male subject, the urethra generally including, in serial order from the externalmost portion to the internal portion, the penile meatus, the penile urethra, the bulbous urethra, the sphincter, the membranous urethra, the prostatic urethra, the bladder neck and the bladder, said prostatic stent comprising:
  a unitary tubular body having a central lumen extending therethrough and a first cross-sectional width thereacross;
  a tissue-engaging inflatable balloon positioned on a lower perimeter portion of said unitary body; and
  at least one conduit having opposing upper and lower end portions with a fluid lumen formed therein, a portion of said upper end attached to said unitary tubular body such that it is in fluid communication with said inflatable balloon, said conduit having a second cross-sectional width the second cross-sectional width being less than said first cross-sectional width; and
  wherein at least one conduit is releasably attached to said unitary tubular body such that it can be detached in situ from the stent by pulling on an end portion of said conduit without dislodging the unitary body from a desired location in the subject; and
  wherein, in position in the subject, said stent is configured such that said unitary body resides above the sphincter and said conduit extends therethrough the sphincter and out of the penile meatus of the subject, and wherein said conduit is sized and constructed such that it allows substantially natural closing of the sphincter when in position in the subject;
  wherein a selected one of said at least one conduits is releasably attached to said unitary tubular body such that it can be detached in situ from the stent by pulling on an end portion of said conduit without dislodging the unitary body from a desired location in the subject, and wherein said selected releasably attached conduit is configured to be readily visually identified externally when said stent is in position in the subject.

* * * * *